United States Patent
Ast et al.

(10) Patent No.: US 10,458,902 B2
(45) Date of Patent: Oct. 29, 2019

(54) ANALYSIS INSTRUMENT, ASSOCIATED SYSTEMS AND METHODS

(71) Applicant: Australian Sensing and Identification Systems Pty. Ltd., Marrickville, New South Wales (AU)

(72) Inventors: Sandra Ast, Marrickville (AU); John Canning, Marrickville (AU)

(73) Assignee: Australian Sensing and Indentification Systems Pty. Ltd., Marrickville, New South Wales (AU)

( * ) Notice: Subject to any disclaimer, the term of this patent is extended or adjusted under 35 U.S.C. 154(b) by 0 days.

(21) Appl. No.: 15/759,565

(22) PCT Filed: Jun. 13, 2016

(86) PCT No.: PCT/AU2016/000203
§ 371 (c)(1),
(2) Date: Mar. 13, 2018

(87) PCT Pub. No.: WO2017/041129
PCT Pub. Date: Mar. 16, 2017

(65) Prior Publication Data
US 2019/0154566 A1    May 23, 2019

(30) Foreign Application Priority Data

Sep. 13, 2015  (AU) .................................. 2015903722
Jan. 5, 2016   (AU) .................................. 2016900022
May 4, 2016    (AU) .................................. 2016901647

(51) Int. Cl.
*G01J 3/46*     (2006.01)
*G01N 21/25*    (2006.01)
(Continued)

(52) U.S. Cl.
CPC ......... *G01N 21/251* (2013.01); *A61B 5/1455* (2013.01); *A61B 5/6898* (2013.01);
(Continued)

(58) Field of Classification Search
CPC ........ G01N 21/25; G01N 21/27; G01N 21/17; G01N 33/52; G01N 35/02; G01N 35/04;
(Continued)

(56) References Cited

U.S. PATENT DOCUMENTS 6,197,257 B1  3/2001  Raskas
7,339,673 B2  3/2008  Roman
(Continued)

FOREIGN PATENT DOCUMENTS

EP     2781910 A1      9/2014
WO  2014/094442 A1     6/2014
(Continued)

OTHER PUBLICATIONS

International Search Report for Application No. PCT/AU2016/000203 dated Aug. 10, 2016 (4 pages).
(Continued)

*Primary Examiner* — Abdullahi Nur
(74) *Attorney, Agent, or Firm* — Michael Best & Friedrich LLP

(57) ABSTRACT

Disclosed is an analysis component and associated systems and methods. The analysis component can be used with an electronic device equipped with a detector for detecting light. The component comprises: a sample holder for holding the sample; a detector site at which a detector, or a detector portion of the electronic device, is to be positioned to detect light reflecting off the sample; and a structural component spacing the sample holder from the detector site by a predetermined distance; wherein the lysis component is configured to allow light from a light source to illuminate the
(Continued)

sample such that light reflected by the sample can be received by the detector for analyzing the sample. An associated system comprises the analysis component and a detector for detecting light reflected off the sample. An associated method comprises providing said system, positioning the analysis component with respect to the electronic device such that the detector, or the detector portion of the electronic device, is placed at the detector site; inserting a sample into the sample holder; illuminating the sample with a light source; focusing an optical system of the detector such that an image of at least a portion of the sample is formed on a detecting plane of the detector; using the detector to receive light reflected off the sample; and analyzing the received light to determine a composition of the sample.

20 Claims, 12 Drawing Sheets

(51) Int. Cl.
*A61B 5/00* (2006.01)
*A61B 5/1455* (2006.01)
*G01N 21/84* (2006.01)
*G06T 7/90* (2017.01)
*G01N 21/27* (2006.01)
*G01N 33/52* (2006.01)
*A61B 5/15* (2006.01)

(52) U.S. Cl.
CPC ......... *A61B 5/7225* (2013.01); *G01N 21/255* (2013.01); *G01N 21/27* (2013.01); *G01N 21/8483* (2013.01); *G01N 33/52* (2013.01); *G06T 7/90* (2017.01); *A61B 5/0033* (2013.01); *A61B 5/150358* (2013.01); *G06T 2207/10024* (2013.01); *G06T 2207/10048* (2013.01); *G06T 2207/30004* (2013.01)

(58) Field of Classification Search
CPC .......... G01N 15/06; G01N 15/14; G06T 7/00; G06T 7/40; G06T 7/90; H04N 5/225; H04B 1/3888; H04M 1/02
See application file for complete search history.

(56) References Cited

U.S. PATENT DOCUMENTS

| | | |
|---|---|---|
| 2006/0222567 A1 | 10/2006 | Kloepfer et al. |
| 2013/0177993 A1 | 7/2013 | Reynolds et al. |
| 2013/0203043 A1 | 8/2013 | Ozcan et al. |
| 2013/0248695 A1 | 9/2013 | MacIntyre et al. |
| 2014/0038206 A1* | 2/2014 | Holmes .................. G01N 21/17 435/7.21 |
| 2014/0072189 A1 | 3/2014 | Jena et al. |
| 2014/0120563 A1 | 5/2014 | Ozcan et al. |
| 2016/0290916 A1* | 10/2016 | Ben Shoshan ......... G01N 15/06 |
| 2016/0327473 A1* | 11/2016 | Ozcan ................ G01N 33/1813 |

FOREIGN PATENT DOCUMENTS

| | | |
|---|---|---|
| WO | 2014/183026 A1 | 11/2014 |
| WO | 2015087232 | 6/2015 |

OTHER PUBLICATIONS

International Preliminary Report on Patentability for Application No. PCT/AU2016/000203 dated Mar. 9, 2017 (13 pages).
Search Report issued from the European Patent Office for related Application No. 16843291.2 dated Apr. 23, 2019 (7 Pages).

* cited by examiner

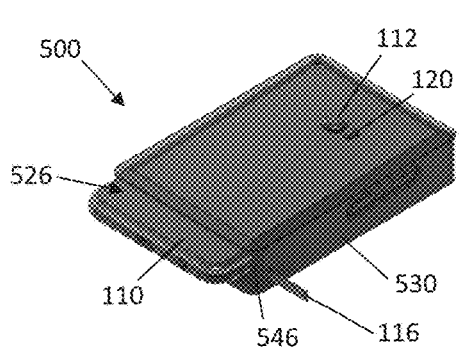
FIGURE 5A
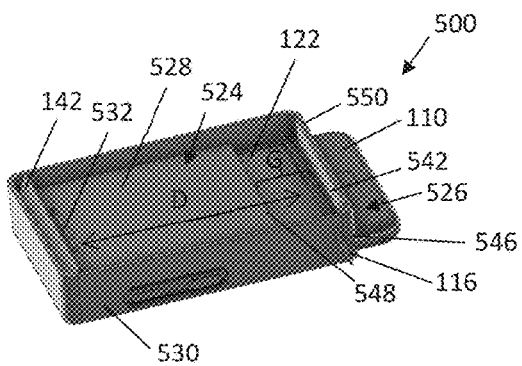
FIGURE 5B
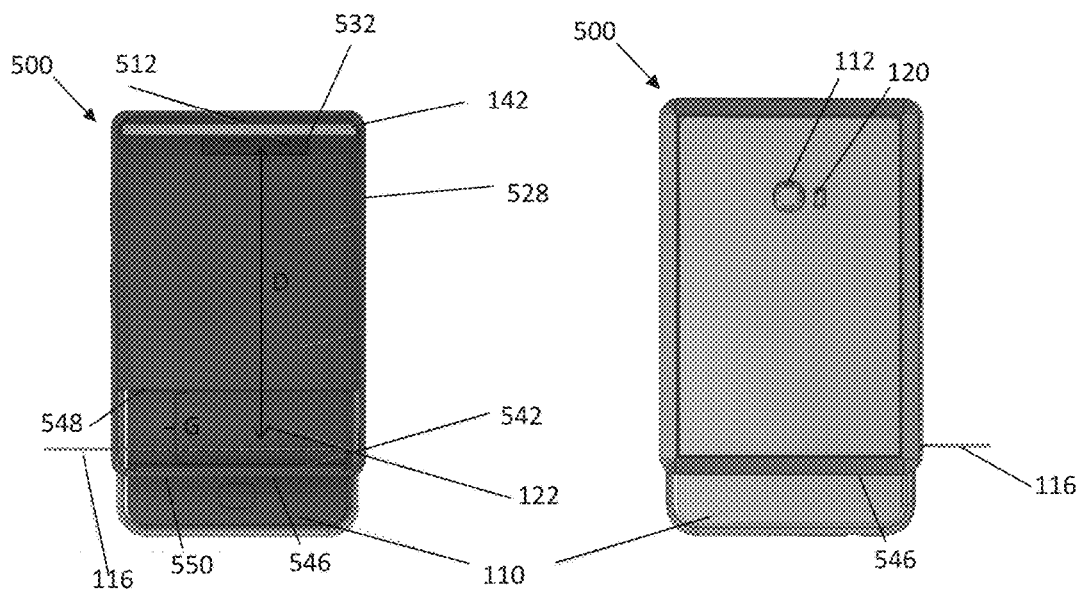
FIGURE 5C
FIGURE 5D

ANALYSIS INSTRUMENT, ASSOCIATED SYSTEMS AND METHODS

FIELD OF TECHNOLOGY

The present disclosure relates to an instrument for smart analysis, the instrument including an analysis component and a smart device such as but not limited to smartwatches, smart catches, smart shoes, a hand-held electronic device, tablets, smart belts, smart gloves, smart glasses, smartphone, cellphone, mobile phone, iPads, smart fridges, smart televisions, and more. The present disclosure also relates to the analysis component itself and related methods.

BACKGROUND

Smart devices such as smart phones and tablets are becoming increasingly prominent in everyday life. Other devices are beginning to be accepted including smart glasses and smart domestic products. The increasing use of smart devices not only arises because they are typically portable and equipped with wireless communication to promote connectivity with other devices, but also because smart devices are commonly equipped with signal detection and processing capabilities. For example, it is common for smart phones to have an in-built camera and run programs to analyse an image captured by the camera.

The growing use of smart devices has lead towards a realisation of their usefulness in various industries. For example, in the health and fitness industry, smart phones may be used to keep track of an individual's fitness routine. As another example, in the music industry, smart phones may be used to record and compile sounds.

More recently, the potential for smart devices as a diagnostic tool in the healthcare industry has been proposed, especially as the concept of personalised healthcare takes shape.

SUMMARY

In a first aspect, the present invention provides an analysis component and/or instrument for use with a smart device, a hand-held smartphone device as example, equipped with a detector for detecting light, the component comprising:
  a sample holder for holding the sample;
  a detector site at which a detector, or a detector portion of the electronic device, is to be positioned to detect light reflecting off the sample; and
  a structural component spacing the sample holder from the detector site by a predetermined distance;
  wherein the analysis component is configured to allow light from a light source to illuminate the sample such that light reflected by the sample can be received by the detector for analyzing the sample.

The analysis component may be remotely operated by the smartphone by Bluetooth® wireless technology, SONAR, free space optics, or other means of remote operation or wireless communication.

The structural component of the analysis component may be configured to space the sample holder from the detector site by the predetermined distance or range of distances such that, in use, the sample is detected at or near a focal length of an optical system associated with, or forming a portion of, the detector. An auto focusing system can relax the requirements on distance.

Enabling the detector to capture an image of the sample at around the focal length of the optical system of the detector can allow for the advantage of more accurate measurements to be taken. This is especially important to quantify results from otherwise previously visualisation based diagnostics.

According to an embodiment, the component/instrument may be used in a manner wherein a detecting plane of the detector (i.e. the part of the detector comprising sensors), or a detecting plane of the detector portion of the electronic device, faces away from the sample holder. In a further embodiment, the component may be used such that the detector or portion thereof faces in a direction substantially 90° away from the sample holder.

The analysis component may comprise an optical arrangement configured to divert light reflected off the sample held by the sample holder toward the detector site. The optical arrangement may comprise one or more mirrors. A mirror may be a reflective structure that reflects light and/or heat at any wavelength. A mirror may also be a diffractive structure such as a grating. A mirror may be any object that redirects light including but not limited to bent waveguides. The mirror can be a flat mirror or a curved mirror. The mirror may be positioned at an acute angle with respect to the detector site. Alternatively, or additionally, the optical arrangement may comprise a lens.

The detector site may comprise a window located in a wall of the analysis component. Further, the analysis component may comprise a divider that, in use, isolates the sample holder from the hand-held electronic device. The structural component spacing the sample holder from the detector site may be part of the divider. The detector site may be defined within the divider. The divider may further comprise an opening area for allowing a light source from the device to illuminate the sample.

The sample holder may comprise at least two sample-receiving elements each capable of receiving a sample and being positioned at different distances with respect to the detector site. The at least two sample-receiving elements may be in the form of elongate grooves within a structural component of the sample holder.

The analysis component may comprise an attachment member for detachably securing the analysis component to the hand-held electronic device. The attachment member may comprise a surrounding wall, wherein a portion of the surrounding wall is resilient and configured to detachably engage around an edge of the electronic device. Further, the attachment member may comprise a surrounding wall having a slot for receiving at least an end portion of the hand-held electronic device including the detector. According to these and other embodiments, the analysis component may thus provide the advantage of being able to fit, attach to, or otherwise be used with any sized phone, tablet or other device.

At least a portion an inner surface of the surrounding wall may extend about the sample holder and may comprise one or more optical components for enhancing illumination of a sample at the sample holder. The one or more optical components may direct light from the illumination source towards to the sample holder.

The analysis component may comprise a reflecting grating positioned with respect to the sample holder such that in use when the sample is illuminated, an image of the sample is projected onto the reflection grating, thus forming a spectrum of the image to be analysed.

The depth of the analysis component may be of smaller dimension than both the length and width of the analysis component.

The analysis component may comprise a compartment for storing samples.

The electronic device may be a hand-held device, which may integrate a smart device, such as a smart phone or a tablet (or iPad etc.), or a wearable smart device such as a smart watch, smart clothes, smart belt etc.

The electronic device may be a smart device, such as a smart phone or a tablet (or iPad etc.), or a wearable smart device such as a smart watch, smart clothes, smart belt etc.

According to a second aspect, the present invention provides a system for analysing a sample, comprising:

The analysis component according to the first aspect; and a detector for detecting light reflected off the sample.

The system may comprise a smart device in which a software application is installed for diagnostics using specific processing such as a line scan, wavelength complement line-scanning and more.

The analysis component and smart device may thus be one combined device standing as a scientific instrument or independent diagnostic instrument. The smart device may act as the inbuilt computer and/or component of the instrument. The independent instrument may contain other components including electronic circuits, optical components and chip sets (e.g. Arduino™ chips, Raspberry Pi™ computing device). The independent instrument may further be operated by or otherwise communicate with a second smart device by Bluetooth™ radio communication device, SONAR or other wireless communication. It may also communicate to a SONAR linked cloud service or other technology that receives SONAR. In one embodiment SONAR can be used to bridge computers, devices and components in a local network. In another embedment SONAR may function better in water environments.

In another example, radio frequency identification (RFID) chips can be used to separate and process data and operate the system through wireless communication independently of the smartphone, e.g. from a remote location. RFID chips also provide for signal identification of devices. Arduino™ devices at times comprise RFID chips.

In another example, optical communications may be utilised. In one embodiment this may be coupled to an optical fibre sensor system. In another embodiment free space optical communications maybe utilised such as between two smart devices communication by detecting modulated LED and/or laser emission. This is particularly useful for direct communication where secrecy and privacy is needed.

According to an embodiment, a portion of sample holder and the structural component may define a first plane, and a detecting plane of the detector may be substantially parallel to the first plane.

The detector may be a detector of a hand-held electronic device arranged to transfer information relating to the detected light to a further electronic device configured to analyse the detected light.

The system may comprise a hand-held electronic device for use with the analysis component and the detector may be a detector of the electronic device.

The electronic device may be configured to analyse the detected light reflected off the sample.

The electronic device may be configured to analyse an image of the sample formed by the detected light reflected off the sample.

According to an embodiment, the analysis component and the electronic device each have a longitudinal axis, and the component may be positioned with respect to the electronic device such that the longitudinal axis of the component is substantially parallel with the longitudinal axis of the device.

Alternatively, according to another embodiment, the analysis component and the electronic device each have a longitudinal axis, the component may be positioned with respect to the electronic device such that the longitudinal axis of the component is substantially perpendicular to the longitudinal axis of the device.

The electronic device may comprise a light source for illuminating the sample such that the detector detects light from the light source reflecting off the sample.

The system may further comprise a light emitting diode (LED) for illuminating the sample such that the detector detects light from the LED reflecting off the sample.

The electronic device may comprise a user-interface on a front surface and an opposing back surface, wherein the analysis component is positioned such that the detector site bears against the back surface.

Alternatively, the hand-held electronic device may comprise a user-interface on a front surface and an opposing back surface, wherein the analysis component is positioned such That the detector site bears against the front surface. The user-interface may comprise an illuminating screen capable of illuminating the sample such that the detector detects light from the screen reflecting off the sample. Further, the analysis component may extend over a portion of the user-interface so that a remaining portion of the user-interface can be used while the analysis component is in place.

The electronic device in the system may be arranged to process the spectrum resulting from the reflection grating and produce a comparison of light intensity and wavelength based on the spectrum. According to some embodiments, the electronic device may be arranged to analyse individual colours separated by the reflection grating.

The detector of the system may detect infra-red light reflected off the sample, or alternatively visible light reflected off the sample.

According to a third aspect, the present invention provides a method of analysing a sample, comprising:
  providing an analysis component having a sample holder for holding the sample and a detector site at which a detector, or a detector portion of the electronic device, is to be positioned to detect light reflecting off the sample;
  positioning the analysis component with respect to a electronic device equipped with a detector for detecting light, such that the detector, or a detector portion of the electronic device, is placed at the detector site;
  inserting a sample into the sample holder;
  illuminating the sample with a light source;
  focusing an optical system of the detector such that an image of at least a portion of the sample is formed on a detecting plane of the detector;
  using the detector to receive light reflected off the sample; and
  analysing the received light to determine a composition of the sample.

A calibration procedure may be performed against differences in electronic devices by using a reference such as a line reference or colour reference. This may be, but is not limited to, the test strip previously mentioned and/or an incorporated intensity reference, colour reference, colour RGB separate references, or colour chart. Thus the method may comprise performing calibration of the detector on an internal or external colour reference or on a standard or reference sample prior to or after inserting the sample into the sample holder. The method may comprise combinations thereof.

The method may further comprise communicating information regarding the received light to a further electronic device in order for the further electronic device to analyse the received light.

The step of analysing the received light may be done by the electronic device. The electronic device may be a hand-held electronic device.

The step of analysing the received light may be done by an optical device. The optical device may be a hand-held optical device.

The method may further comprise forming an image of the sample using the detected light.

The step of analysing the received light may comprise performing colorimetric analysis on the image of the sample. The colorimetric analysis may comprise obtaining red-green-blue (RGB) values of the image of the sample.

Alternatively, the colorimetric analysis may comprise obtaining hue-saturation-value (HSV) values of the image of the sample.

The step of positioning the analysis component may comprise attaching the analysis component to the electronic device.

Prior to the detector receiving light reflecting off the sample, the method may comprises positioning the analysis component on a flat surface such that the component is between the hand-held electronic device and the flat surface.

The method may comprise illuminating the sample from behind in order to project an image of the sample onto a reflection grating to produce a spectrum of the sample to be analysed. It will be appreciated that the back illumination is not limited to the spectral analysis and can also be used for the colorimetric applications in order to achieve an evenly distribute illumination and avoid reflections.

The method may comprise filtering a portion of the light reflected from the sample prior to the detector receiving light reflecting off the sample. The filter may be in the form of a transparent container of a gaseous substance through which at least a portion of the light reflected off the sample can travel.

The method may comprise electronic or photonic processing of the signal to simulate a reference.

The electronic device may be a smartphone or tablet or any smart device including but not limited to smart watches, smart belts, smart fridges, smart television, smart patch, smart hat, smart glasses, smart car. The method may comprise using a light source of the smartphone or tablet to illuminate the sample, or using an illuminated user-interface of the smartphone or tablet to illuminate the sample.

Alternatively, the method may comprise using a light emitting diode to illuminate the sample.

The step of inserting a sample into the sample holder may comprise inserting a vessel containing bodily fluid or tissue to be analysed. Alternatively, the step of inserting a sample into the sample holder may comprise inserting a vessel containing a sample of a person's breath to be analysed.

According to embodiments of the disclosed method, immediate data collection is performed by a software application which may facilitate image capture of the sample. A secondary process may analyse that image data.

In one embodiment, rapid collection of data may involve but is not limited to use of an application that performs line scanning in a single direction in the case of line test strips or two directions in the case of square test strips. In a further embodiment his line scanning may involve separate line scanning for RGB components which may improve signal to noise by adding or subtracting or performing other functions between each RGB component data.

Also disclosed is an analysis application to be implemented on a smartphone, tablet or other smart device, and method of processing the data, where the processing involves a particular approach for a particular application. This approach may be instantaneous and/or time based, monitoring the evolution of a sample such as disease or infection over time (but not limited to). This temporal dependence can provide information of the rate of spread of a disease and therefore can be useful for biomedical mapping and analysis over the internet. It is an example of an IoT capability of this instrument.

It is noted that for the purposes of this disclosure, the term "colour" includes all wavelengths such as, but not limited to visible light, infrared light, near infrared light and UV light.

Also disclosed is a method of analysing a sample, comprising:

providing an analysis component having a sample holder for holding the sample and a detector site at which a detector, or a detector portion of the electronic device, is to be positioned to detect light reflecting off the sample;

positioning the analysis component with respect to a an electronic device equipped with a detector for detecting light, such that the detector, or a detector portion of the electronic device, is placed at the detector site;

inserting a sample into the sample holder;

illuminating the sample with light in the red, green or blue spectral bands of visible light;

using the detector to receive light reflected off the sample; and analysing the received light to determine a composition of the sample.

The method may comprise focusing an optical system of the detector such that an image of at least a portion of the sample is formed on a detecting plane of the detector.

BRIEF DESCRIPTION OF DRAWINGS

Embodiments of the present invention will now be described, by way of example, with reference to the accompanying drawings in which:

FIGS. 5A and 5B are perspective views of an analysis component in use according to another embodiment.

FIG. 5C is a front view of the analysis component, shown in FIGS. 5A and 5B.

FIG. 5D is a back view of the analysis component shown in FIGS. 5A and 5B.

DETAILED DESCRIPTION

Figure 1:
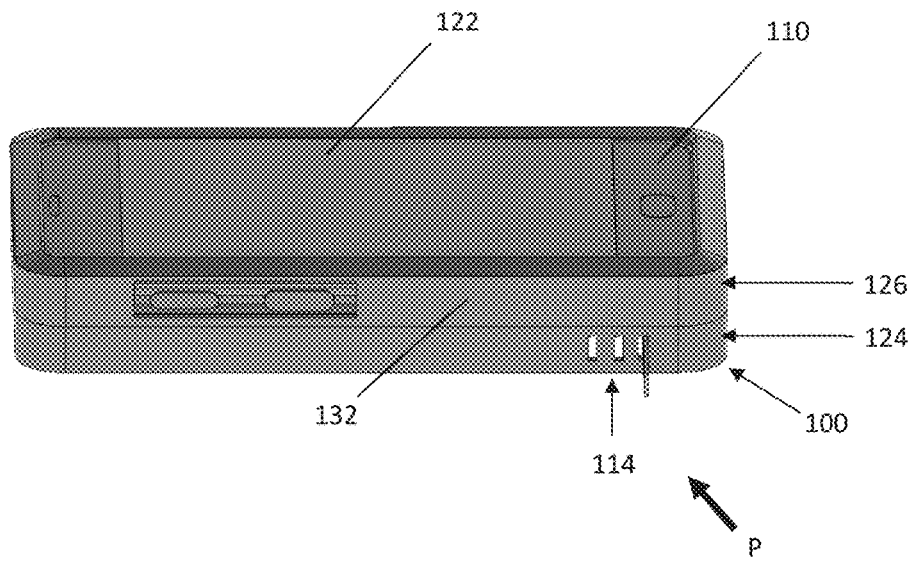
FIG. 1 is a side perspective view of an embodiment of an analysis component being used with a hand-held electronic device.
Figure 2:
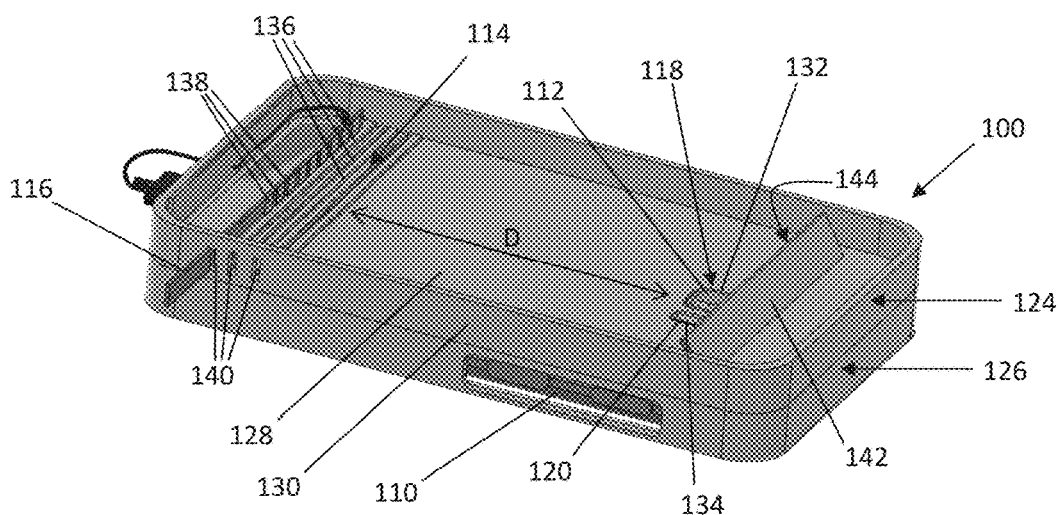
FIG. 2 is a perspective view of the analysis component shown in FIG. 1 from perspective "P".

Referring to FIGS. 1 and 2, there is shown an analysis component 100 for use with a hand-held electronic device 110 equipped with a detector 112 for detecting light. In this embodiment, the hand-held electronic device is a mobile phone or smartphone 110 and the detector is an in-built camera 112 of the smartphone. The analysis component 100 comprises a sample holder 114 for holding a sample 116, a detector site 118 at which the camera 112 (or a portion thereof, such as an outer lens) is to be positioned, and a structural component spacing the sample holder 114 from the detector site 118 by a predetermined distance "D". The analysis component 100 is further configured to allow light from a light source to illuminate the sample 116. The light from the light source can therefore be reflected off the sample 116 and received or captured by the detector or camera 112 for the purposes of analysing the sample 116. In this embodiment, the light source is an in-built camera flash 120 of the smartphone that cooperates with the camera 112.

In other words, in this embodiment the analysis component 100 provides a structural arrangement for the camera 112 of a smartphone 110 to capture an image of the sample 116 for further analysis. The electronic device or smartphone 110 may be configured to then analyse the detected light reflected off the sample. In this embodiment, the detected light forms an image of the sample 116 displayable on a display 122 of the smartphone 110. The image can then be processed by an appropriate program or application installed in the smartphone or other computing device, for instance, utilising colorimetric analysis techniques.

Throughout the specification, the term "colorimetric analysis" or variants thereof refers to a method of quantitatively or qualitatively assessing the composition of an analyte in a chemical sample based on the detected colour or change in colour of the sample. The colour detection or colour change may be in, but is not limited to, the visible, ultra-violet, near-infrared or mid-infrared parts of the electromagnetic spectrum.

Also, throughout the specification, the term "detector" refers to any device, equipment, instrument or component thereof, which operates in a manner that detects or senses the presence of something, such as an object, substance or form of energy. For example, in this specification, a camera is considered to be a detector because it operates by detecting or sensing light reflected of an object.

To provide context, it is known to utilise colorimetric or reagent test strips in medical and other applications, which change colour depending on the concentration or composition of an analyte in the sample applied to the test strip. Such testing also has application in, but is not limited to, the agricultural and food industries, industrial safety, and defence, e.g. to guard against biological weapons. The test strip is then typically compared to a colour chart to provide an indication of the analyte concentration or composition. Embodiments of the invention facilitate colorimetric analysis of an analyte in a sample by providing an analysis component that holds the sample in a desired position while a device suitable for colorimetric analysis captures an image of the sample to assess its colour.

With further reference to the analysis component 100 shown in FIGS. 1 and 2, according to this embodiment the analysis component comprises a first portion 124 dedicated to facilitating analysis of the sample and a second portion 126 for attaching the component 100 to the smartphone 110.

In this embodiment, the second portion 126 is dimensioned to receive the smartphone 110 in a manner that encases the smartphone 110 while leaving the display 122 visible and exposed for a user to interact with. In particular, the second portion 126 comprises a surrounding side wall 132 configured to engaged a surrounding edge of the smartphone. The side wall 132 may be resilient to facilitate fitting of the second portion 126 to the smartphone 110.

The component further comprises a divider in the form of a partition wall 128, as well as a peripheral wall 130. The partition wall 128 lies between, and thus divides the analysis component 100 into, the first and second portions 124 and 126. The partition wall 128 effectively serves to isolate the sample holder 114 and thus the sample 116 from the smartphone 110. In use, if the smartphone display 122 is taken to be the front of the smartphone 110, the first portion extends from the back of the second portion 126.

The peripheral wall 130 extends from and is perpendicular to the partition wall 128. The peripheral wall surrounds a region of the analysis component 100 dedicated to the sample analysis, including the sample holder 114 and the detector site 118. The peripheral wall 130 is aligned with the surrounding wall 132 and the walls 130 and 132 can therefore be regarded as a single, integrated wall. Accordingly, the component 100 comprises similar length and width dimensions to the smartphone 110. Thus, the depth of the analysis component 100 is of smaller dimension than both the length and width of the analysis component. This may provide the advantage of an ergonomic and compact design.

With particular reference to FIG. 2, in this embodiment, the detector site 118 comprises a window or opening 132 located in the partition wall 128. The window 132 may be located at any position along the optical path length. In this embodiment, the window 132 is sized and positioned such that the camera 112 located on the back of the smartphone 110 aligns with the window 132 when the smartphone 110 is received in the second portion 126. Similarly, in this embodiment a further window or opening 134 is located in the partition wall 128 at a position that aligns with the flash 120 associated with the camera 112.

The sample holder 114 comprises a plurality of sample-receiving elements in the form of elongate and preferably parallel grooves 136 for receiving the sample 116. The sample 116 in accordance with this embodiment is in the form of a strip or test stick comprising a plurality of test pads 138 (e.g. 9 to 12), or alternatively test lines, to which an analyte is applied. It will be appreciated that the sample base, i.e. anything to which an analyte is applied or received for the purposes of the analysis, may come in different shapes or forms other than as a strip.

Multiple test pads also allows for multiple instances of the same test to build up statistical credibility. Alternatively, multiple test pads allow multiple tests to be undertaken simultaneously. The test pads may comprise different reagents to test for different analytes or properties of analytes. In particular urine test strips can test for different properties, e.g. blood, pH, ketone, protein, cortisol etc., at the same time to provide a holistic assessment. In another embodiment, multiple test pads can facilitate multiple field measurements at different times from various parties in situations where a common ailment disease may be present.

More specifically, each groove 136 spans substantially a width of the partition wall 128 and is configured to receive an elongate edge of the test strip, thus holding the sample 116 at a desired location. The sample holder 114 further includes a plurality of sample ports 140 in the form of openings located in the peripheral wall 130 aligned with one or more grooves 136. In use, the test strip 116 can be placed in the sample holder 114 by insertion through one of the sample ports 140 and sliding into a corresponding groove 136, as shown in FIG. 2. When placed in the sample holder 114, the test pads 138 of the test strip 116 face towards the window 132 and thus the camera 112. The plurality of grooves allow for the samples to be placed at different distances with respect to the camera 112.

It will be appreciated that with this particular arrangement shown in FIG. 2, although the grooves 136 and the camera window 132 are substantially in the sample plane, in use the camera 112 of the device 110 points in a direction perpendicular to the test pads 128. In other words, the detector site is configured such that a detecting plane (i.e. an array of sensors) of the detector at the detector site 112 points or faces away from the sample holder, and preferably substantially 90° away from the sample holder 114. The detecting plane is therefore parallel with the partition wall 128 in which the grooves 136 and detector site 118 reside. Accordingly, in order for the camera to capture an image of the test pads 138, the analysis component 100 further comprises an optical component in the form of a mirror 142 to direct the light reflecting off the test pads 138 towards the camera 112. The mirror 142 in this embodiment is an elongate mirror that spans substantially a width of the partition wall 128.

In particular, the mirror 142 is positioned near the camera 112 at an acute angle with respect to the partition wall 128 such that a reflecting surface 144 of the mirror faces partially towards the test pads 138 as well as the camera 112. The sample holder 114 and the mirror 142 are thus placed substantially at opposite end portions of the first portion 124 of the analysis component 100, such that the test pads 138 and reflecting surface 144 somewhat face each other. The camera window 132 is placed between the sample holder and the mirror 142 but closer to the mirror 142, which is angled towards the camera, for example, between 45° and 60° with respect to the partition wall. It will be appreciated that if the flash 120 is placed near the camera 112, light from the flash 120 will also be directed towards the sample via the mirror 142.

Accordingly, in use, a user inserts a test strip 116 into one of the grooves 136 and takes a picture with the camera 112 of the smartphone 100. As the picture is taken, the flash 120 operates to illuminate the sample and cause light to reflect off the test pads 138 and travel along a length of the smartphone towards the reflecting surface 144 of the mirror 142, which in turn directs the light towards the camera 112. As a result, the camera 112 captures an image, particularly a colour, of the test pads 138, which can be further analysed using colorimetric techniques.

A significant advantage of the invention according to this and other embodiments is that the camera window 132 (and thus the camera 112) is spaced from the sample holder 114 (and thus the sample) by a predetermined distance "D" that allows the camera 132 to capture an image of a sample at or near the focal point of the camera 132. It is known for smartphone cameras to have a focal length of around 24 mm to 30 mm, similar to the distance "D" between the sample holder 114 and window 112. Thus, the portion of the partition wall 128 between the sample holder 114 and window 112 may be considered the structural component of the analysis component 100 that spaces the sample holder 114 from the detector site 118.

By placing the sample 116 at or near the focal point of the camera 112, embodiments of the present invention can improve the imaging of a sample and subsequent signal processing by the smartphone 110 or other device equipped for digital calorimetric analysis. Conversely, not having the sample at the focal point will create variations in colour values, which will then reduce reproducibility of the result.

Use of the mirror 142 to bend the light reflected from the sample 116 towards the camera also provides the advantage of allowing the sample 116 to be imaged at or near the focal point of the camera 112, while avoiding a need for the sample to be placed directly in front of the camera 112. Accordingly, in use, the first portion may be placed along a length of the phone, thus providing a compact design and ergonomic design, as well as user friendliness.

In addition, since smartphones and their cameras vary between manufacturers, by having multiple parallel grooves 136 positioned at different fixed distances with respect to the detector site 118, a user can adjust the distance between the sample 116 and the camera 112 to better suit the focal point of the particular camera by moving the sample to another groove closer to or further away from the camera window 132.

In use, the analysis component 100 attached to the smartphone 110 may be positioned in the manner shown in FIG. 1, with the peripheral wall 130 on a flat surface, in order to block off the majority of outside light while the image is being captured. In this position, a user can also operate the phone using the user interface 122 or screen to, for example, operate the camera and view the results of the analysis. Alternatively, the component 100 may comprise a removable cover, such as a hinged lid attached to the peripheral wall 130, to close off the first portion 124.

Embodiments of the invention also provide the advantage of avoiding or reducing the likelihood that the sample will contact smartphone during the whole analysis process, which may be undesirable for some samples, for example if the sample comprises urine or blood. Accordingly, the partition wall 128 separates the sample holder 114 from the smartphone 110 such that the sample 116 only contacts the first portion 124 of the analysis component 100. Further, in some embodiments, the first portion 124 and second portion 126 are detachable from each other, thus allowing for the first portion 124 to be separated for cleaning. Alternatively, the first portion 124 (or the whole component) may be disposable, and therefore can simply be discarded after use and replaced with another first portion.

Further embodiments of the invention will now be described with reference to FIG. 3 onwards. Similar reference numerals will be used for features that are the same as or similar to features in FIGS. 1 and 2.

According to another embodiment, another way of adjusting the bath length is to use an optically transparent but high index block, which may be placed between the sample and detector.

Figure 3:
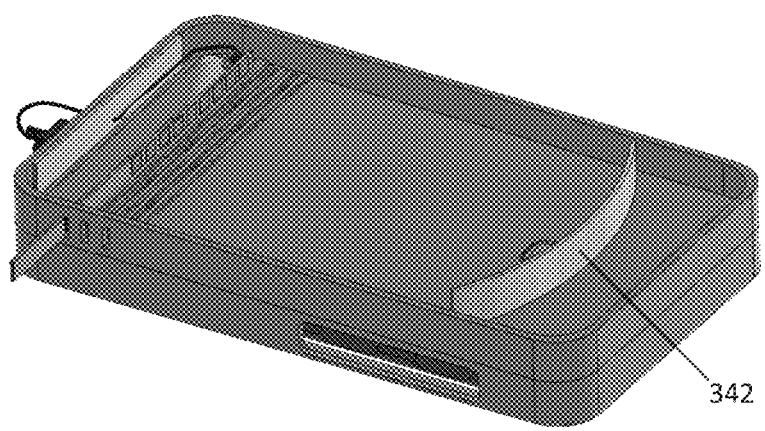
FIG. 3 is a perspective view of the analysis component according to another embodiment.

According to another embodiment, instead of the mirror 142, FIG. 3 shows a curved mirror 310. 7. The use of a bent or curved mirror may be particularly beneficial to fit, longer test strips or strips that have more test pads into the imaging window.

Consistent lighting conditions are desirable whenever illuminating the sample 100 in the analysis component to optimise the accuracy of results. For instance, more consistent lighting conditions may be achieved by scattering or filtering out unwanted light, and thus improving the signal-to-noise (SNR) ratio with respect to the light signals detected by the detector or camera. Various optical components can be used to achieve such optimisation, such as mirrors, reflection gratings, multi-pass optics and/or waveguides.

As another example, a fan material designed to scatter unwanted light away from the detector or camera, or surfaces angled away from the detector, may be utilised to achieve more consistent lighting conditions. Such unwanted light may for example come from back reflection off surfaces. Additionally or alternatively, periodic scattering points, sites or areas on the interior surface of the first portion 124 to diffuse light and ensure an even illumination may be utilised.

Figure 4:
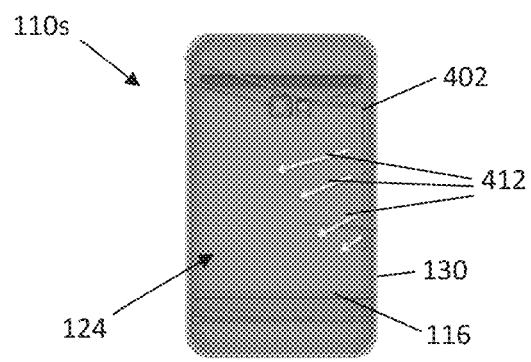
FIG. 4 is a front view of an analysis component in use according to another embodiment.

For example, with reference to FIG. 4, in one embodiment, improved lighting conditions may be achieved via light scattering within the interior of the second portion 124. Here, a light pipe or optical waveguide 408 is attached to an inside of the peripheral wall 130 of the first portion 124 of the analysis component 110s, to release light 412 in varying quantities along a length of the peripheral wall 130 to achieve a more even illumination of light on the sample 116. The light pipe 408 can be 3D printed so that they can be made very small. Alternatively, reflectors on the inside of the peripheral wall may be used to enhance illumination of the sample.

Barriers placed in appropriate locations can also reduce the excitation light from reaching the camera 112. For example, a barrier may be placed between the light source and the camera 112 to reduce excitation light. Similarly, a barrier may be placed on a side of sample where light might scatter towards camera 112.

Another technique of filtering out unwanted light and thus optimising the accuracy of colorimetric readings is to use optics, such as multiple waveguides, to isolate or "select" particular colours from the test strip (i.e. filter out other colours) and imaging directly onto the detector or camera. This may provide faster measurements and also reduce signals received by the detector 112 from other wavelengths that may not be relevant to the desired measurements. This may also remove additional unwanted light scattered from around the test areas on the strip. For example, a green filter will allow only green light to reach the detector, so that the measurement of green light signal is not diluted by background light.

A simple aperture designed to match the particular test strip can be used to block out unwanted light scattered from the test strip areas. As another non-limiting example, near-IR transmission filters may be used to allow near IR-light to transmit and to reduce all visible wavelengths. Visible wavelengths typically have a higher signal generation on detector in comparison to near-IR and will therefore produce unwanted background signal, thus will reduce the SNR ratio.

Another approach to divert unwanted light away from the detector site is to use multiple foci such that only light following the correct trajectory is collected at the foci. Yet another approach is to use etalon based filters to tighten the required path length to reach the detector or camera.

According to another embodiment, instead of using the camera flash 112 of the smartphone or other electronic device to illuminate the sample, a connectable illumination device, such as a light emitting diode (LED) may be provided. Using an LED as an alternative to the camera flash 120 can minimise additional light scatter. By virtue of their spectrum, LEDs are already "filtered" relative to white light, so for some tests this will provide better SNR ratio. The hand-held electronic device may be equipped with the LED, or the LED may be provided as a separate component to the electronic device. Alternatively or additionally, the LED may be provided as part of the analysis component.

Figures 10A, 10B:
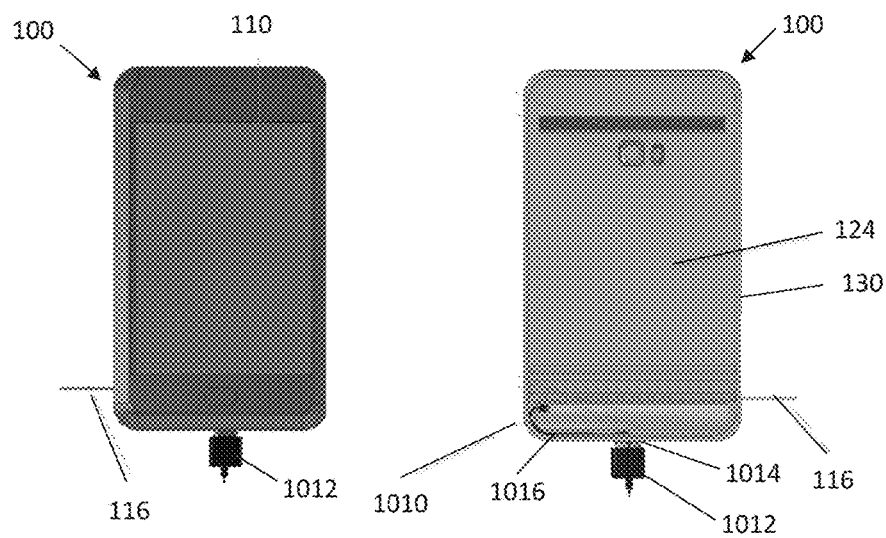
FIG. 10A shows a front view of an illumination device used with an analysis component in accordance with an embodiment.
FIG. 10B shows a back view of the illumination device used with the analysis component shown in FIG. 10A.

For example, with reference to FIGS. 10A and 10B, the LED device 1010 may comprise a connector 1012, such as a USB (universal serial bus), micro-USB, lightning or thunderbolt connector, or other suitable connector. The connector 1012 is located at one end of the device 1010 and is connectable to a corresponding input socket 1014 of the smartphone 110 for drawing power for the LED from the smartphone. The device 1010 further comprises an elongate wiring portion 1016 and an LED at an opposite end to the connector 1012. The peripheral wall 130 of the analysis component 100 may be provided with an opening through which the LED end of the device 1010 can pass to access the interior of the first portion 124 in order to illuminate the sample 116. In the embodiment shown in FIG. 10, the LED is placed in close proximity to the sample.

The LED may operate as a flash LED when the camera 112 captures an image of the sample and/or as one that provides constant illumination. Other specialty LEDs might be used in various applications such as one that emit a particular colour of light, exciting fluorescence or for near-infrared (IR) wavelength probing. For example, a green LED may be used to illuminate a sample in order to highlight colour contrast with a red sample. In another example, UV light may be used to excite green fluorescence. In other examples, which will be discussed later on, near-IR and mid-IR may be used in certain applications.

With reference to FIGS. 5A to 6C, according to further embodiments of the present invention, the analysis component 100 is configured to cooperate with a smartphone 110 or other portable device such that the screen of the smartphone 110 is utilised for illumination. FIGS. 5A and 5D show an analysis component 500. Features of the component 500 that are similar to the analysis component 100 are labelled with like reference numerals.

One of the main differences between component 500 and component 100 is that instead of partition wall 128 spanning the full length of the component 100, the wall 528 of component 500 spans a portion of the length of the component 500 and terminates at edge 542, leaving a gap "G". The wall 528 nevertheless serves to separate a first portion 524 dedicated to capturing an image of the sample, from a second portion 524 for receiving the smartphone 110.

Another main difference is that instead of the surrounding edge of the smartphone 110 being fully received within the surrounding side wall 132 of the second portion 126 of component 100, a peripheral wall 530 of the component 500 comprises a slot 546 at an end portion 550 of the component 500. The slot 546 has a width that allows the smartphone 110 to slide upper-end first into the second portion 526 of the component 500. Specifically, the slot 526 allows the smartphone 110 to be received in the component with its screen 122 facing towards the wall 528.

By virtue of the above differences, the component 500 allows for a screen 122 of the smartphone to illuminate the first portion 524 of the component through the gap "G". Additionally, it is common for smartphones to comprise a screen camera 512 on the front of the smartphone 110 as well as the camera 112 on the back of the smartphone 110 previously discussed. Accordingly, with this arrangement, since the smartphone 110 is now facing towards the first portion 524, the screen camera 512 may now be utilised to capture images of the sample 116 as the screen 122 illuminates the sample. In this regard, a window 532 is also provided in the wall 528 through which the screen camera 512 can view the sample 116 with the assistance of an angled mirror 142.

The embodiment shown in FIGS. 5A-D provides the advantages of having a larger illumination source (the smartphone screen 122), which is also closer to the sample 116.

According to another aspect of the present invention, there is provided a system comprising the analysis component herein described and an electronic device that the analysis component can be used with. The electronic device may be a hand-held electronic device. The electronic device may be a smart device, such as a smartphone or tablet. Such smart devices may be equipped to perform colorimetric analysis on the analysed sample. Alternatively, the smart device may be equipped to transfer information regarding the image of the sample captured to another device, such as a bench top computing device, equipped to analyse the image. In yet another alternative, the electronic device may be a camera or other device That can detect such as an IR reader, which can then be equipped to transfer information regarding the detected light to another device capable of performing the colorimetric analysis. In one embodiment, the analysis component and electronic device forms a single, integrated device.

Figures 6A, 6B:
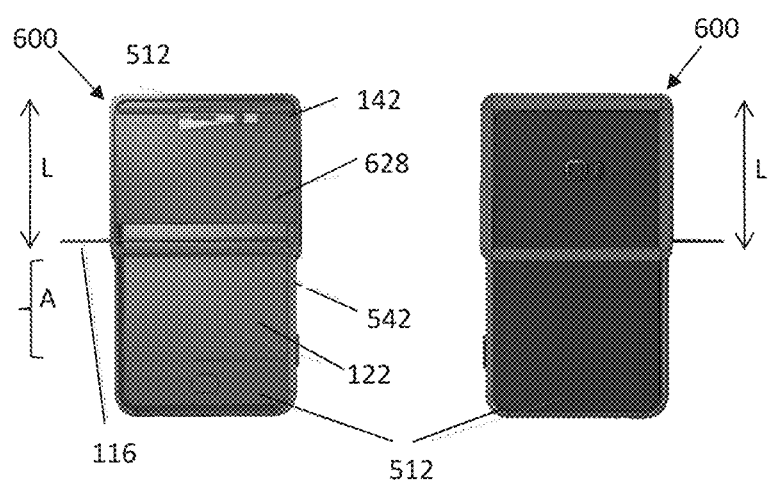
FIG. 6A is a front view of an analysis component according to another embodiment.
FIG. 6B is a back view of the analysis component shown in FIG. 6A.
Figure 6C:
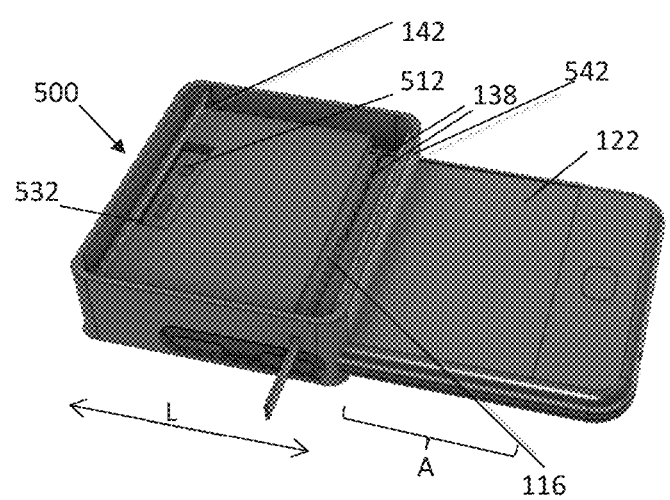
FIG. 6C is a perspective view of the analysis component shown in FIGS. 6A and 6B.

Turning now to FIGS. 6A-C, another embodiment of an analysis component 600 is shown. Like component 500, the embodiment shown in FIGS. 6A-C is configured such that the screen 122 of the smartphone 110 can be utilised to illuminate the sample. The main difference to the component 500 is that the overall length "L" of the component 600 is shorter than the component 500.

Thus, in use, while the component 500 overlies most of the screen area 122 of the smartphone 110, the component 600 overlies approximately half of the area of the screen 122. Accordingly, an area "A" of the smartphone screen 122 remains outside of the component 600 when in use. This provides the advantage that a user of the smartphone 110 can continue to use a portion of the screen (area A) even while the smartphone 110 is received in the component 600. Therefore, the screen 122 of the smartphone 110 can be effectively divided to perform different functions: illumination of the sample; and a user interface.

According to an embodiment, three RGB diodes can be used separately in different parts of the screen to perform different excitations for different species.

In FIGS. 6A and 6C, according to a further embodiment, it is noted that a reflection grating 542 is positioned on an inner surface of the end portion 550 of the component 500, and the test pads 138 of the sample 116 faces towards the grating 542. A reflection grating causes a dispersion of light incident on it to produce a spectrum. In this embodiment, the test strip 116 can be illuminated from behind, for example by light from the screen 122 and projected onto the reflection grating 542, thus producing a spectrum of the sample 116. An image of the sample spectrum is then reflected on the mirror 142 and can be captured by the camera 512. The image can then be processed using an appropriate software application on the smartphone to plot the intensity over wavelengths. The resulting peaks of the plot can then be selected and compared with a database of known peak characteristics in order to determine the composition of the sample. The electronic device may be arranged to analyse the individual colours separated by the reflection grating. In another example, due to the shorter distance of the test strip to the detector in this setup, it may be necessary to use a mirror instead of the grating 542. The grating 542 or mirror is thus positioned such that it reflects onto mirror 142. Alternatively, the reflection grating 542 may be replaced with a mirror and the mirror 142 may be replaced with reflection grating. If the path length is long enough to reach the focal lengths without the second mirror (i.e. the grating 542) then this can be removed and just the grating next to the camera is needed and the strip would face towards the mirror/grating 142.

Prior to taking a measurement, an unused test strip may first be imaged so that the measurement can be compared to a standard. Alternatively, a colour reference can be used for this calibration step. The colour reference can be part of the test strip or part of the device. An example of a calibration process will be described in more detail later.

According to this embodiment, by allowing for the sample spectrum to be imaged and plotting intensity over wavelength, more accurate identification of the composition of the sample can be obtained, since compounds and element have a unique intensity spectrum. It will be appreciated that this reflection grating arrangement can be implemented in other embodiments of the invention.

Embodiments of the invention provide an analysis component with the advantage of allowing direct measurement of samples. Therefore, the testing of samples other than in the form of a test strip is contemplated. In this regard, the sample holder of the analysis component may be specifically configured for other forms of sample. For example, the sample ports 140 and grooves 136 of the sample holder 114 may be modified to receive a transparent tube, vial or other appropriate vessel containing a solid, liquid or gas.

Embodiments of the invention also provide the advantage of making it possible for types of colorimetric analysis other than those that involve the detection of colour or a colour change in the visible light spectrum, since solid, liquid and gas samples can be analysed. Many compounds have distinct IR bands or are UV active alone and could be determined directly by detection and comparison against a database of known characteristics. Therefore, the use of detectors other than those that predominantly detect visible light is contemplated. For example, near-IR, mid-IR and UV detectors may be used.

Accordingly, in some embodiments of the invention, the electronic device may be an IR or UV detector. Such detector may itself by equipped for colorimetric analysis, or at least be configured to transfer information (wired or wirelessly) regarding the detected signals to another device capable of conducting colorimetric analysis. Alternatively, a smart device may be incorporated with an IR detector.

According to another aspect of the present invention, there is provided a system comprising the analysis component herein described and an electronic device that the analysis component can be used with. The electronic device may be a smart device, such as a smartphone or tablet. Such smart devices may be equipped to perform colorimetric analysis on the analysed sample. Alternatively, the electronic device may be a camera or other device that can detect light, such as an IR reader, which can then be equipped to transfer information regarding the detected light to another device capable of performing the colorimetric analysis. In one embodiment, the analysis component and electronic device forms a single, integrated device.

Another advantage provided by some embodiments of the present invention is the suitability of the analysis component to be used with various kinds of electronic devices regardless of their shape, size and configuration. In this regard, the analysis component may comprise a flexible attachment part or member that serves to secure the analysis component onto a smart device. The flexible attachment part may for example be the second portions 126 and 526 of the components 100 and 500, respectively, as they are dedicated to receiving the smartphone 110. The flexible nature of the second component may assist in accommodating for smartphones of different sizes. The first portion 126 or 526 may be rigid or flexible. The analysis component can be manufactured via 3D printing since flexible filaments for 3D printers are available.

Figure 7:
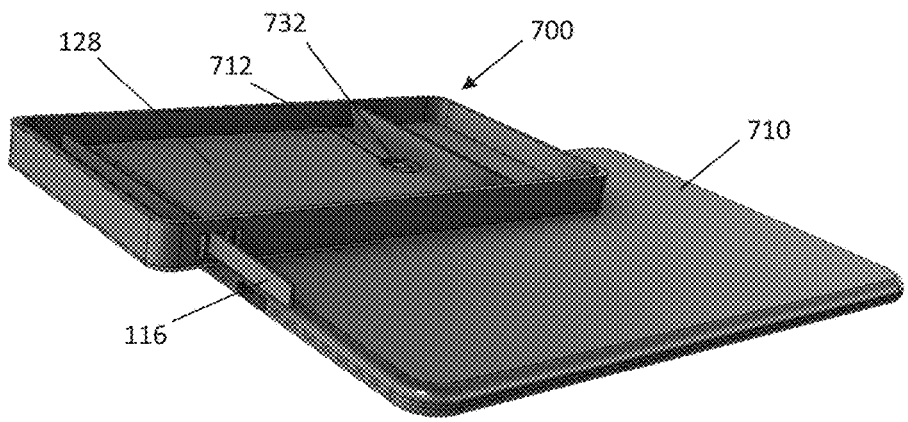
FIG. 7 is a perspective view of an analysis component, in use, according to yet another embodiment.

Alternatively, with reference to FIG. 7, according to an embodiment, the analysis component does not comprise a second portion dedicated to receiving part of the electronic device. Rather, in his embodiment the analysis component 700 effectively comprises only the first portion 124 of component 100. Since the component 700 is no longer limited co use with devices than fit within an attachment part such as the second portion 126, the component 700 is free to be positioned anywhere with respect to the device, such as a tablet 710 equipped with a camera 712.

Significantly, the camera window 732 of analysis component 700 is free to be positioned at the exact location of the camera 712 of the tablet 710 in order to capture an image of the sample 116. Optionally, the component 700 may also be provided with an attachment member, such as a clip, or a suction cup or temporary adhesive on an outside surface of the wall 128, to detachably secure the component 700 to the tablet 710 when in use.

Figure 8A:
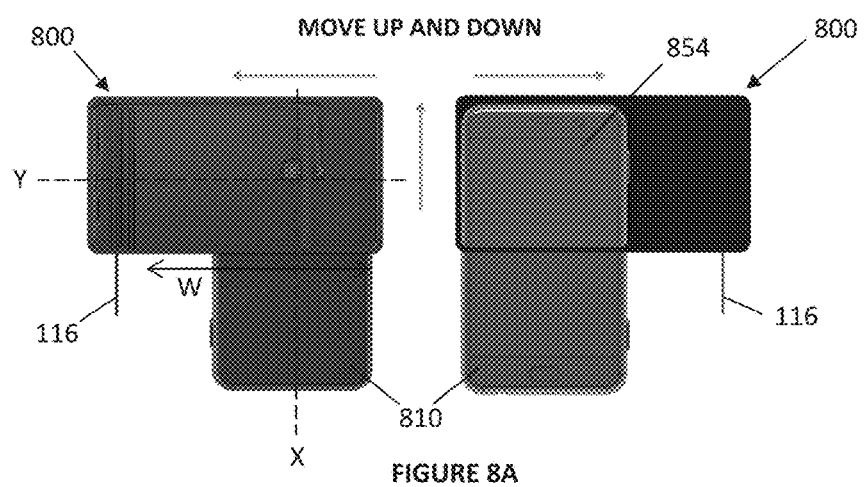
FIG. 8A a back view (left) and a front view (right) of an analysis component according to yet another embodiment, illustrating how the position of the analysis component can be adjusted with respect to a device.
Figure 8B:
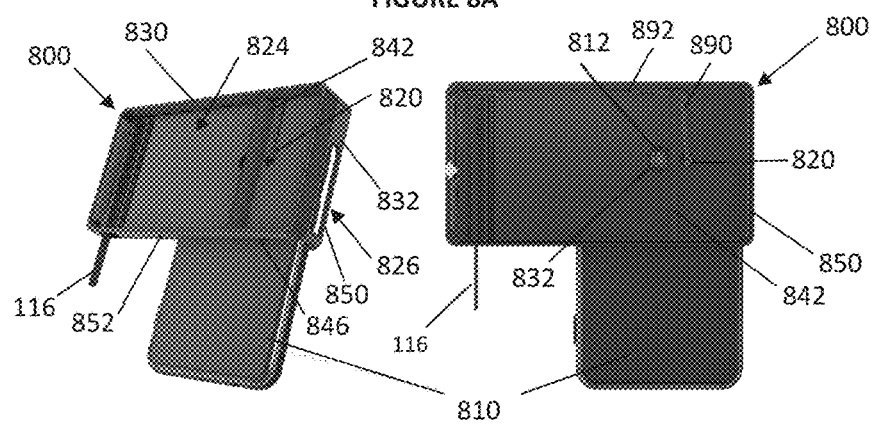
FIG. 8B shows a perspective view (left) and a back view (right) of the analysis component shown in FIG. 8A.

FIGS. 8A and 8B show yet another embodiment of an analysis component 800. In this embodiment, the component 800 is similar to the component 500 in that it comprises a first portion 824 for capturing an image of the sample 116, a second portion 826 dedicated to receiving the smartphone 810, and a slot in the surrounding wall 832 for receiving the smartphone. However, unlike the component 500, a slot 846 is provided in a side portion 852 of the surrounding wall 832 instead of or in addition to a slot being provided in an end portion 850. Thus as shown in FIGS. 8A and 8B, an upper portion 854 of the smartphone 810 can be inserted through the slot 846 in the side portion 852 to be received in the component 800. In other words, the analysis component 800 is configured to receive a smartphone 810 in a manner such that a longitudinal axis "X" of the smartphone is perpendicular to a longitudinal axis "Y" of the component 800. Further, the width of the slot "W" extends beyond the width of the smartphone 810. Therefore, in use, the component 800 can move with respect to the smartphone 810 as indicated by the directional arrows "R", "L" and "U". This provides the advantage of allowing for the camera window 832 to be positioned at the exact location of the smartphone camera 812 to account for variations across different smartphone designs.

Furthermore, in this embodiment shown in FIGS. 8A and 8B, the component 800 also comprises a light pipe 890 operatively connected at one end to the camera flash 820 of the smartphone 810. The other end of the light pipe 890 is disposed near the sample 116, and more specifically behind the sample 116, in order to direct light from the flash to an area in the vicinity of the sample to provide better illumination of the sample. An elongate mid portion 892 of the light pipe 890 may be disposed within the first portion 824 but away from the line of sight of the camera to the sample. For example, as shown in FIG. 9, the mid portion 804 is attached to an inner surface of the peripheral wall 830. It is also noted that the mirror 842 in this embodiment is positioned between the flash 820 and camera 812 of the smartphone 800.

Figures 9A, 9B:
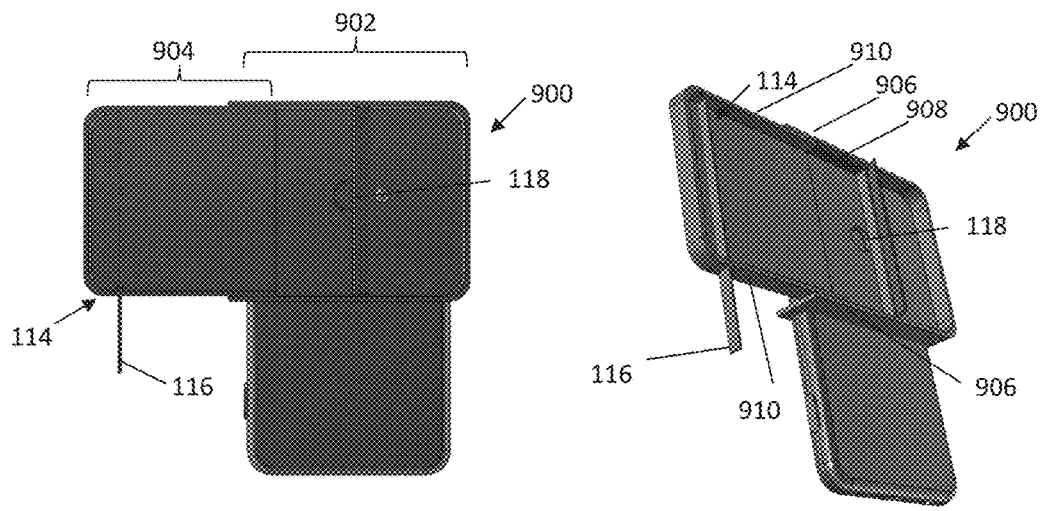
FIG. 9A shows a front view of an analysis component according to yet another embodiment.
FIG. 9B shows a perspective view of the analysis component shown in FIG. 9A.

With reference to FIGS. 9A and 9B, in accordance with yet another embodiment, an analysis component 900 may comprise two Parts that are movable with respect to each other. The component 900 is similar to the component 800 shown in FIGS. 8A and 8B. However, in this embodiment a first part 902 may be configured to receive or otherwise removably attach to the smartphone, and a second part 904 may be linearly movable or slidable with respect to the first part 902 along a longitudinal axis of the component 900. In this example, such movement is enabled by the inner surface of side walls 906 of the first part comprising elongate grooves or guide lines 908 to receive complementary portions on the outer surface of side walls 910 of the second part 904. Accordingly, the distance between the sample holder 114 and sample 116 from the detector site 118 is adjustable.

According to yet another embodiment, a method of sterilising an interior of the analysis component is disclosed, including but not limited to using temperature or UV light or combinations thereof e.g. from a UV LED to sterilise against germs and bacteria and viruses. Another alternative is to use plastics designed to have some antibiotic or antibacterial property. A sterile environment is necessary for medical applications but also in other areas of application in order to avoid cross contamination, which would impede the accuracy of the measurements. More sterile materials better customised for specific applications might be used, such as silica based holders. Also, antibacterial coatings may be used with various embodiments of the analysis component. This can be done either during the 3D printing process by using antibacterial filaments or afterwards by adding an antibacterial coating, for example, using an antibacterial coating spray. Additionally, water-repellent (hydrophobic) surface coatings may be used to wipe clean or to apply antibacterial sprays onto the component after use. Various embodiments of the analysis component may also comprise a water-repelling surface to allow for easy cleaning and avoid cross contaminations of substances on the sample. This can be done using appropriate composition materials, laser processing or structured materials.

According to another embodiment, the analysis component contains an extra compartment for storing test strips for practical reasons. This compartment meets the correct conditions, i.e. a temperature range between 2-30° C., and presence of a drying agent, such as silica to avoid moisture. A thermocouple or other temperature sensor may, in use, be disposed inside the analysis component to monitor temperature.

As another example of how more accurate measurements can be obtained by embodiments of the analysis component, it is recognised that the colour change is dependent on the temperature during the measurements. Thus, temperature control can add another level of accuracy and sensitivity in colorimetric sample analysis, particularly if the response at different temperatures can enhance higher resolution determination. In this regard, various embodiments of the disclosed analysis component may use insulating hardware material that allows for maintenance of temperature of the sample within a certain range and shielding from extreme heat and cold. Examples of suitable insulating material include foam and porous plastics. The porous plastics may be in filament form, which can be 3D printed. The foam may be spray insulation foams.

Avoiding temperatures above 30° C. and below 0° C. may provide for better storage of the test strips and may guard against the decomposition of certain dyes used in test strips or other samples for colorimetric analysis. The temperature control can also be achieved by the incorporation of active heating or cooling elements such as Peltier devices, nichrome heating wires, fans, etc.

As another example, a sample receptacle, such as a cuvette, can be made of porous material such as silicone or other polymer, which has pore size channels comparable to human skin (~1 nm), or materials that may be designed for a particular species so it acts like a molecular sieve. Materials that are optically transparent are preferred or the material can be heated up to release the absorbed chemicals for identification within a smart device spectrometer (UV-VIS, or Near IR or mid IR). Changes in sample receptacle properties such as impedance, resistance and/or capacitance can also be used to help monitor the material.

Various aspects of the subsequent analysis of the image of the sample captured by an appropriate detector will now be discussed. As previously mentioned, such analysis may be conducted by the hand-held electronic device, or a separate device that can receive the colorimetric readings from the hand-held device equipped to transfer the readings, e.g. wirelessly.

Firstly, it may be necessary to calibrate the camera of a particular smart device prior to analysis. A reference sample may be imaged for the purposes of calibration, such as a test strip that does not contain an analyte or a different analyte to the one to be tested. The image of the reference can then be compared to a standard colour chart, such as the Munsell Colour System. The analysis program installed on the smartphone or other device may comprise suitable functions, suitable reference charts coded in an algorithm, or directly as an image for comparison to calibrate the camera. The colour chart can be part of the test or can be embedded or otherwise attached to the analysis component for ease of reference.

In relation to the colorimetric analysis, one method is to collect raw RGB data of the sample and process the data (e.g. using an appropriate program) to compare the data against known reference such as the Munsell Colour System. Alternatively, HSV (hue-saturation-value) values may be used instead of RGB. In this regard, RGB values may first be obtained and then converted to HSV, or HSV values can be measured directly. RGB to HSV conversion is an ability common to smartphones. The Hue component of the HSV may then be selected and incorporated into a linear formula.

Figure 12:
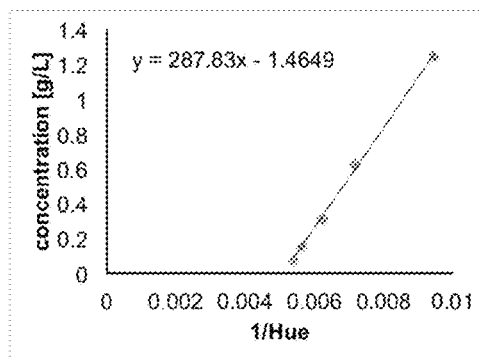
FIG. 12 is an example of a plot of analyte concentration against 1/Hue derived from an HSV value obtained in according with an embodiment.

For example, the analyte concentration may be plotted as a function of 1/(Hue value) to achieve a linear relationship between the analyte and the Hue value. See for example FIG. 12. In this regard, the hue values for the respective analyte concentrations can be measured using solutions of known analyte concentrations (the solutions were prepared to arrive at the particular concentrations).

A resulting calibration formula may then be introduced into a software application used for the colorimetric analysis. The Value component of the HSV value can be used in a similar way, which relates to the Munsell Colour System. A predetermined calibration formula can be used for determining the concentration of the analyte from the Hue value. Calibration formulae are predetermined for all kinds of test strip measurements and can be stored in and accessible from the cloud, stored in an electronic device, or available in a smartphone application.

In other words, the relationship between the sample colour and chemical composition of the analyte may be determined by taking several test points across the range of potential concentrations and applying a curve of best fit. This function can then be integrated into an image processing algorithm with the RGB, HSV and chemical composition outputted as part of the results.

It will be appreciated that the above description is not limited to the use of the Hue value, i.e. Saturation and Value channels from the HSV colour system may be used as well if better suited for the measurement, i.e. if a higher accuracy is achieved. A person skilled in the art can easily determine experimentally which colour value might apply by measuring calibration formulas for each colour value.

According to one embodiment, the "white balance" is locked (in electronic devices that have "auto white balance" functionality, i.e. the camera is automatically acquiring the white balance point) during testing to avoid unwanted signal variations. This is done by imaging of a white sample and thereby setting the white colour to a fixed value for the actual measurement taken in the next step. Alternatively, a (real or virtual) white background colour reference may be used.

Figure 14A:
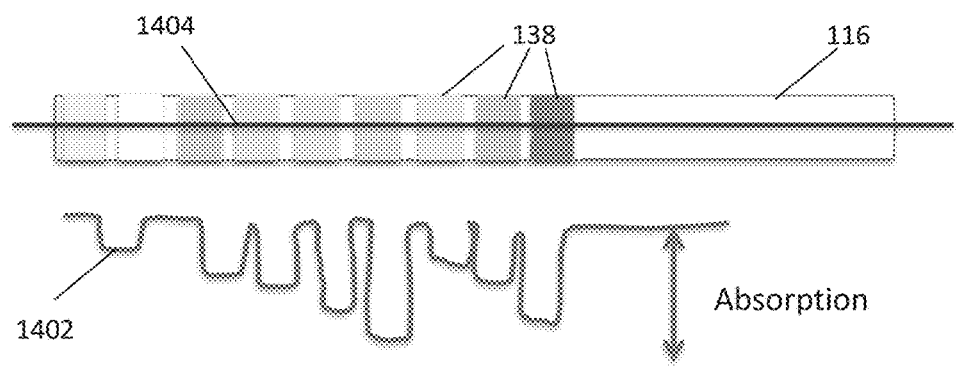
FIG. 14A shows a schematic diagram and an associated line scan of a sample that can be analysed using a system and method according to an embodiment of the invention.
Figure 14B:
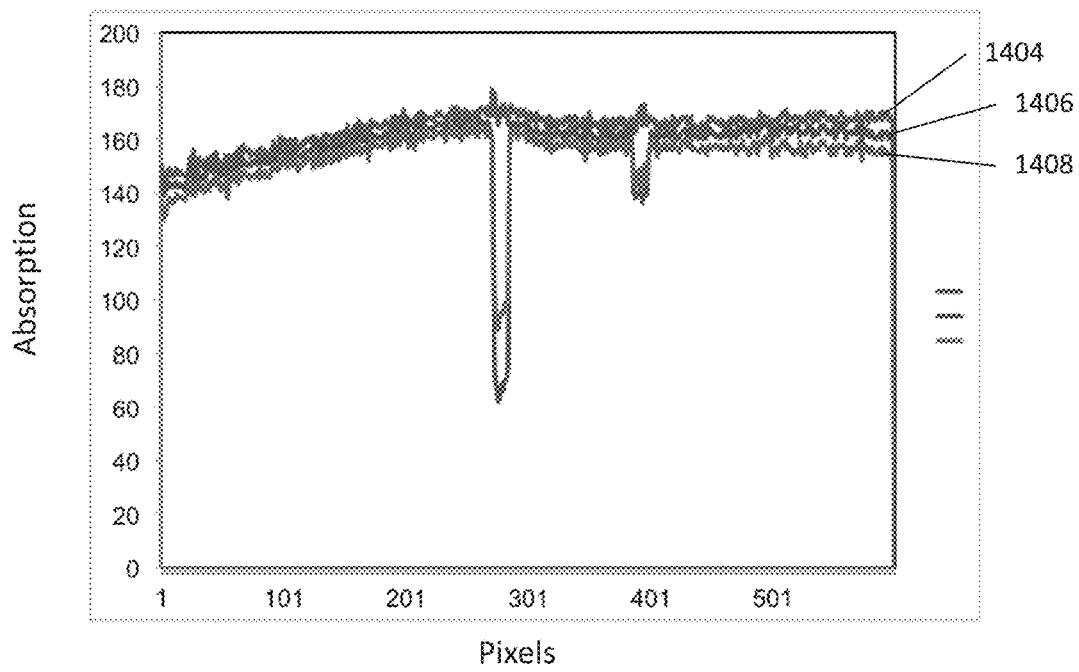
FIG. 14B shows a spectrum associated with the line scan shown in FIG. 14A.
Figure 14C:
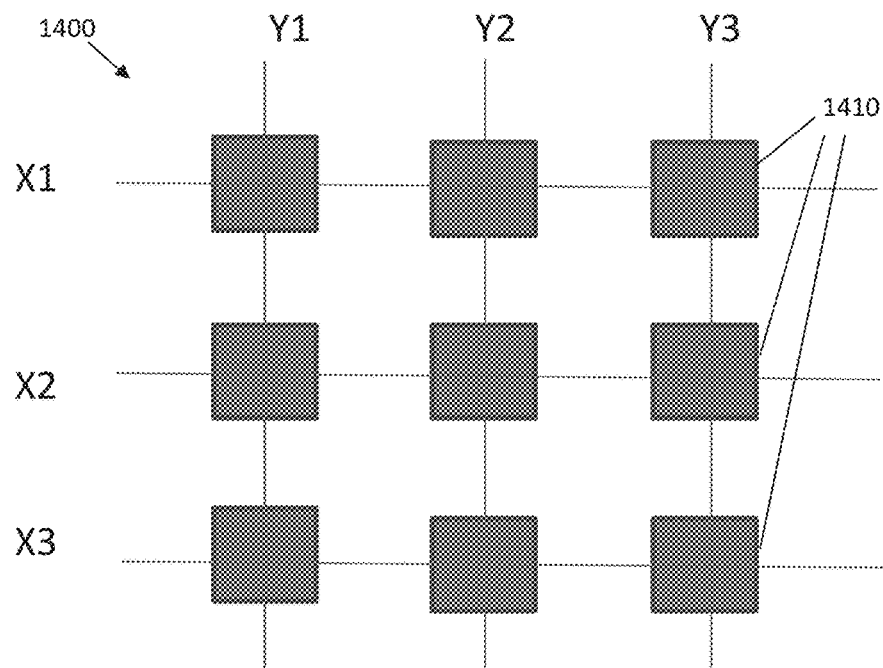
FIG. 14C shows another schematic diagram and an associated line scan of a sample that can be analysed using a system and method according to an embodiment of the invention.

According to yet another embodiment, with reference to FIGS. 14A to 14C, the present invention provides a method and system that facilitates the location of a colour by applying a line scan process to an image of a sample. As previously mentioned, the test strip 116 may comprise test lines or test pads. Locating the imaged colours can be complicated and may otherwise require a comprehensive algorithm; however, according to this embodiment colour location can be largely facilitated by selecting only a small number of pixels (line width, y-direction) and screening across a chosen axis (for example horizontal) of the image thereby forming a "line".

The line scan process may utilise an analysis component herein described and may characterise the image of a test pad or test line (i.e. using the electronic device and suitable algorithm) to compare measurements between test pads or lines. An image of the strip 116 may be captured, a "line" 1404 of pixels is selected from which the individual colour value is recorded as a function of intensity. An example of a plot of these colour values as a function of intensity is shown as line scan 1402 spanning the plurality of test pads 138 (see FIG. 14A). The RGB colours of the image may then be characterised across the sample to obtain a spectra for each component of the RGB—red (1404), green (1406) and blue (1408) within that line—for each test pad or line test, as shown in FIG. 14B.

In one example with particular reference to FIG. 14C, these line scans may be done in X and Y directions on the image, which may be manually collected or automated with the device program. Line scans X1, X2, X3, Y1, Y2 and Y3, thereby pass over each portion 1402 of the sample twice: once in an X-direction (horizontal) and once in a Y-direction (vertical). By scanning each sample portion 1410 in both an X-direction and Y-direction, the point at which each X-direction scan intersects with each Y-direction scan defines a position in the sample portion (i.e. at X1Y1, X2Y1, X3Y1, X1Y2 etc.) with respect to the overall sample. The changes in each colour may differ and can be combined to maximise signal to noise measurements of the data and obtained the relative differences between tests pads.

According to an example, HSV values can then be obtained from those RGB values, which can then be analysed to determine a composition of the sample at each particular area.

The system and method according to this embodiment may be particularly useful for tests such as urine tests and blood tests that require relative intensity measurements, since the quantification of the individual colour values is inherent to the line scan process, i.e. and the resulting data can then be transferred into the appropriate formulas. This embodiment also helps improve SNR.

Figure 15:
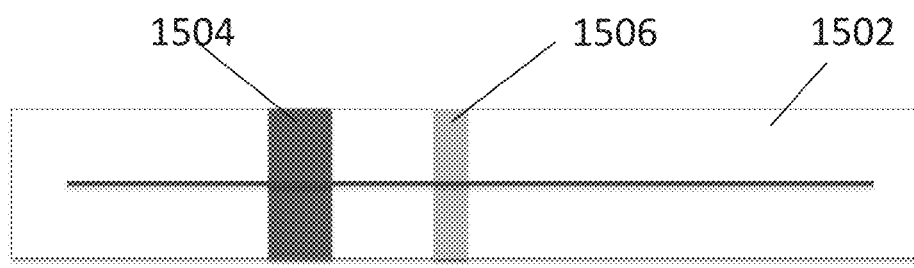
FIG. 15A shows a schematic diagram of a test strip with a sample that can be analysed using a system and method according to an embodiment of the invention.
FIG. 15B shows a schematic diagram of a test strip with a sample that can be analysed using a system and method according to an embodiment of the invention.
Figure 15:
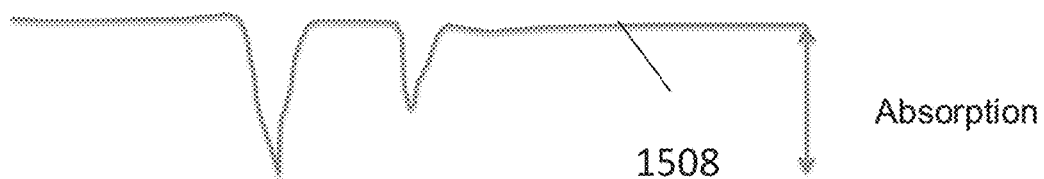
Figure 15:
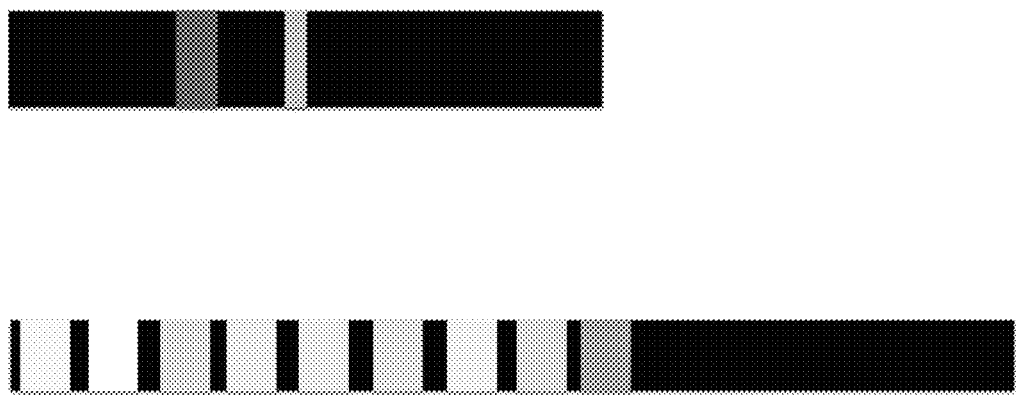

Another application of line scanning techniques is shown in FIG. 15. As discussed earlier, a reference sample, such as a test strip that does not contain an analyte, may be used for the purposes of calibration. In FIG. 15, both a reference sample 1504 and a sample to be tested 1506 are included on a test strip 1502. Thus, as a line scanner scans across the test strip 1502, the associated detector will detect an individual signal response for both the reference sample 1504 and test sample 1506, as shown by the line scan measurement 1508. The samples 1504 and 1506 can therefore be compared with each other for calibration purposes. An example of a formula that can be used for calibration once the line scan reading is obtained is as follows: $C=1-(I_{ref}-I_{sample})/(I_{ref})$; where $C$=relative sample concentration, $I_{ref}$=reference sample intensity, and $I_{sample}$=test sample intensity. As an alternative, as previously mentioned, the measurement line can be calibrated by measuring samples of known analyte concentration.

Also contemplated is the utilisation of satellite and wireless communication capabilities in smart devices or other electronic devices to use the results of the colorimetric analysis further. According to an embodiment, a smart device having a GPS and configured to analyse or store the results of a colorimetric analysis of a sample can then link the results with GPS coordinates of the device. Such coordinates and linked results can then be collected for data processing, for example, by a central server. Such data processing may for instance involve the mapping of analysis results in real-time to allow for monitoring of user data, such as:

Tracking the spread of a disease or contaminant;
Determining a possible outbreak and/or source of a disease or contaminant quickly;
Monitoring health data of populations etc.

Figure 16:
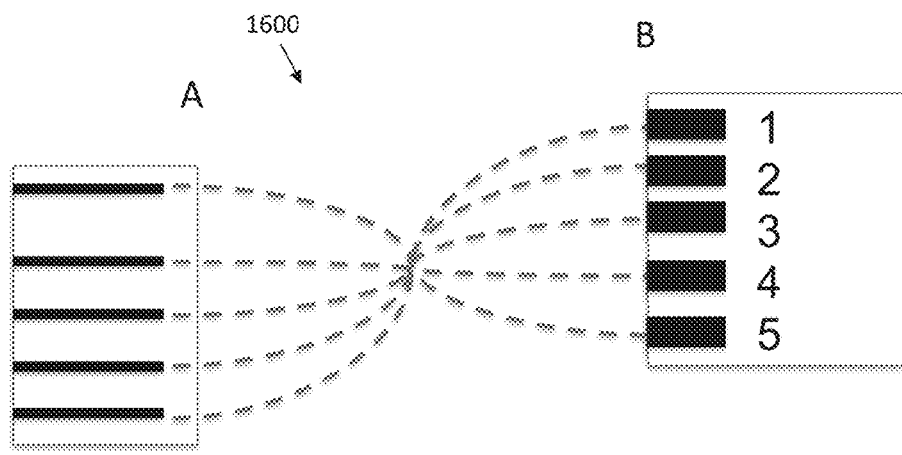
FIG. 16 shows a schematic diagram of invention twistable adaptor.
Figure 17B:
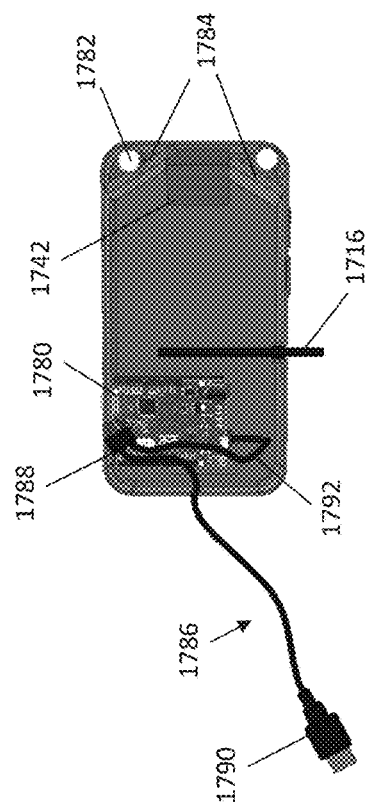
FIG. 17B is a back view of an analysis component of the system in FIG. 17A.
Figure 17D:
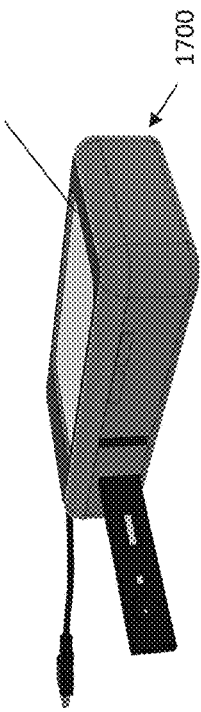
FIG. 17D is a perspective view of the system shown in FIG. 17A.
Figure 17A:
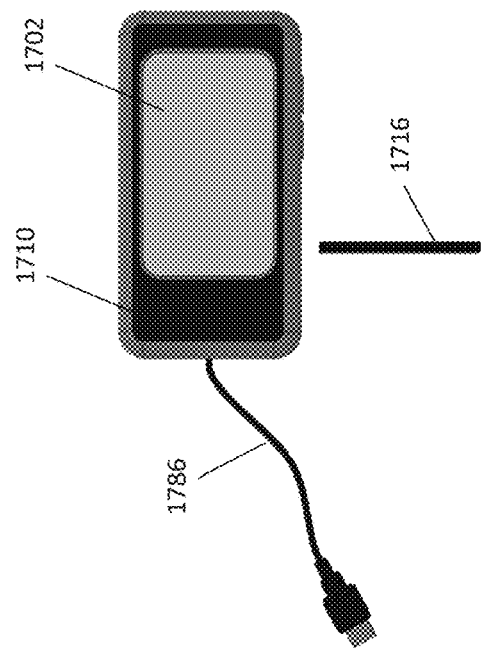
FIG. 17A is a top view of a system according to an embodiment of the invention.
Figure 17C:
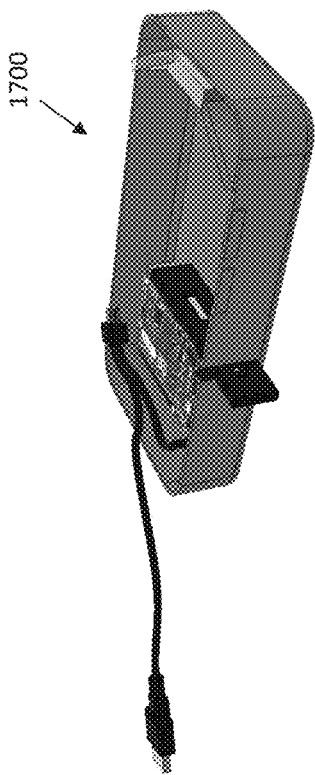
FIG. 17C is a perspective view of an analysis component of the system shown in FIGS. 17A and 17B.

With reference to FIG. 16, also disclosed is a rotating connector or twistable adapter 1600 for embodiments where a detector for imaging the sample is separate to the smartphone or other electronic component. Such a detector, for example FLIR ONE™ infrared cameras for smartphones, may be powered by plugging into a power socket of the smartphone. However, different smartphone designs will have different socket configurations, resulting in variations in the direction faced by a detector with respect an associated the smart device. Accordingly, a rotating connector or twistable adapter is envisioned, to be positioned between and connect the power socket and the detector. The connector 1600 can change the direction in which the detector faces by twisting one end A of the connector with respect to B.

Also disclosed is the use of a unique identifier for different types or brands of test strips. For example, a barcode may be used as the identifier, which can be imaged by the smart device and identified with appropriate software. The barcode or other identifier may be visible or invisible on the test strip, and may for instance by a UV or IR active identifier. This may provide the advantage that certain manufacturers and their calibration charts can be identified, as certain tests may have articular requirements and/or to guard against imitation tests of lesser quality. User identification can also be done, for example, via fingerprint or eye tests.

As previously mentioned, embodiments of the analysis component can be used to facilitate light detection and/or colorimetric and or spectroscopic sample analysis for various applications. Such applications include:

Food contaminants or food testing (wine, milk powder, oil, meat, frozen berries);
Antibiotics;
Food colouring (e.g. chlorophyll, beta-carotene);
Fitness (e.g. hydration status, salts);
Hazardous substance exposure (e.g. benzene, those frequently exposed to hazardous environments can test their exposure levels, for example through urine testing);
Medicines (e.g. authenticity of pills; the sample analysis results can also be shared with doctor and/or pharmaceutical services);
For measurements that require testing over longer time frame (i.e. 24 h urine test)
Analytes in bodily fluids (e.g. urine, blood, saliva, sweat, for presence of a disease or drug testing)
Disease and biohazard testing;
Chemical testing;
Environmental monitoring and mapping;
Water testing (e.g. drinking water or pool);
Metal ion detection (e.g. metal contamination in water);
Agriculture;
Soil testing (e.g. for toxins or nutrition levels);
Chemical weapons (e.g. anthrax);
Cancer testing (for example cervical cancer but in general any cancer test that is based on spectroscopy);
Detection, mapping and/or Internet of Things (IoT) dispersion of the above.

In one example, a specific medical application of an embodiment of the present invention will now be described. In this embodiment, infra-red spectroscopy is utilised.

*Helicobacter pylori* tests are used to detect a type of bacteria in the stomach and upper part of the small intestine that causes ulcers. One of the tests available to detect *Helicobacter pylori* is a urea breath test. *Helicobacter pylori* produces an enzyme called urease, which breaks urea down into ammonia and carbon dioxide. During the test, a substance containing urea (a chemical made of nitrogen and a minimally radioactive carbon) is ingested by the patient and an amount of exhaled carbon dioxide is measured, thus providing an indication of *Helicobacter pylori* in the stomach. The patient's breath may be collected by blowing into a balloon, tube, or other suitable containment means.

More specifically, patients are given a urea $C^{13}H_4N_2O$ sample containing $C^{13}$, which then reacts urease (if present) to produce ammonia and $C^{13}O_2$. The $C^{13}O_2$ can then be detected by various means in order to determine the presence or extent of the infection. For instance, it is noted that "normal" breath has $C^{12}O_2$. The $C^{13}O_2$ product of the reaction absorbs at longer wavelengths to $C^{12}O_2$ in normal breath, so can be differentiated by using for example narrow line-width laser or nuclear magnetic resonance (NMR), which usually takes a few days to get results and can be expensive.

According to certain embodiments of the invention, infra-red spectroscopy is utilised to provide a relatively lower cost *Helicobacter pylori* test using a smartphone or other every computing device, such as desktop or laptop with wireless capabilities. In particular, embodiments of the disclosed analysis component may facilitate the analysis configurations shown in FIGS. 11A-C.

Figure 11A:
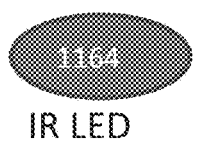
FIGS. 11A to 11C are schematic diagrams of an analysis setup according to various embodiments.
Figure 11A:
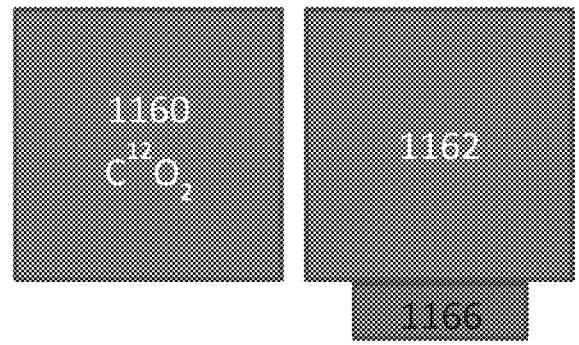

In the schematic diagram shown in FIG. 11A, a $C^{12}O_2$ reference sample 1160 (normal breath) and a sample to be tested 1162 possibly containing $C^{13}O_2$ are collected. The $C^{12}O_2$ reference sample 1160 is placed in front of the test sample 1162 with respect to an infra-red LED source 1164 for illuminating the sample. The LED source may be separate to or provided with the analysis component and may provide collimated IR radiation. An appropriate detector 1166 for detecting the presence of $C^{13}O_2$ is placed relative to the test sample 1160. For instance, an infra-red detector can be used to measure an increase in heat of a sample as a result of the presence of $C^{13}O_2$.

Here, the reference sample 1160 acts as a filter so only the part of the IR spectrum relating to $C^{13}O_2$ reaches the sample 1162. Any $O^{13}O_2$ present in the test sample 1162 will result in absorption. This absorption can be measured a number of ways, for example, directly measuring the absorption (since the wavelength of $C^{13}$ is longer and thus passes through the reference, thus the signal that reaches the detector is proportional to sample absorption), measuring an increase in heat of the sample as a result of the absorption, or an acoustic signal change, with an appropriate detector 1166.

This absorption can be measured, for example, at time t=30 min, which will lead to an increase in signal at the detector 1166. It will be appreciated that there are other ways to enhance that attenuation including using multiple path and ring cavity spectroscopy.

Figure 11B:
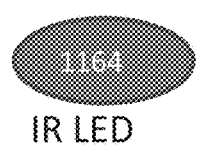
Figure 11B:
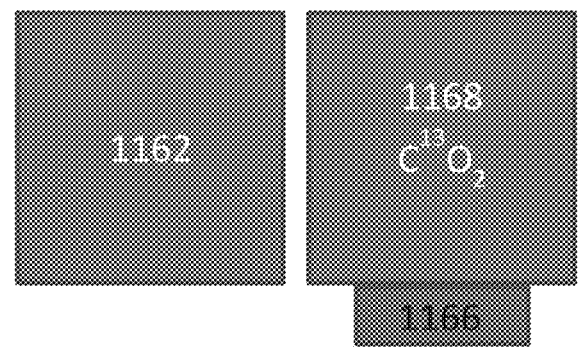

In an alternative setup shown in FIG. 11B, the light passes through the test sample 1162 and then into the $C^{13}O_2$ reference sample 1168. If $C^{13}O_2$ is present in the sample (e.g. at t=30 min) then it will result in attenuation, i.e. reduction in signal strength reaching the detector 1166. Consequently, there is a measured reduction in signal as heat and/or acoustic signal, but an increased apparent absorption at the $C^{13}O_2$ reference sample 1168. It will be appreciated that there are other ways to enhance that attenuation including using multiple path and ring cavity spectroscopy.

Figure 11C:
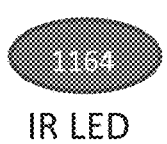
Figure 11C:
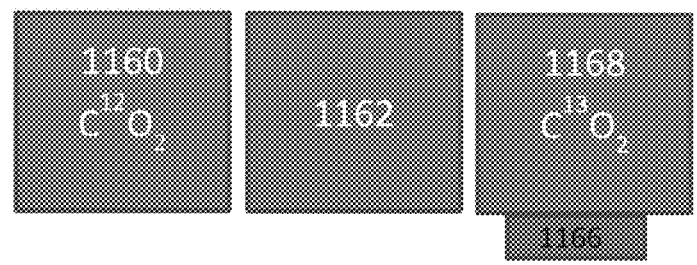

In yet another alternative setup shown in FIG. 11C, a combination of the above techniques of FIGS. 11A and 11B is shown. $C_{12}O_2$ reference sample 1160 acts as a filter, removing the LED portion of spectra so only that for $C^{13}O_2$ reaches sample. Any $C^{13}O_2$ present in test sample 1162 will result in attenuation of signal through the sample. This attenuation is further enhanced at the detector 1166 after the signal passes through the $C^{13}O_2$ reference sample 1168. So for example at time t=0 there is a base level where only natural levels of $C^{13}O_2$ are detected, thus maximum hear or acoustic signal at detector 1166. At time t=30 mins, light reaching $C_{13}O_2$ reference sample 1168 is reduced, so heat and acoustic signals at detector 1166 also reduces, although apparent absorption at the $C^{13}O_2$ reference sample 1168 may increase. It will be appreciated that there are other ways to enhance that attenuation including using multiple path and ring cavity spectroscopy.

Figure 13:
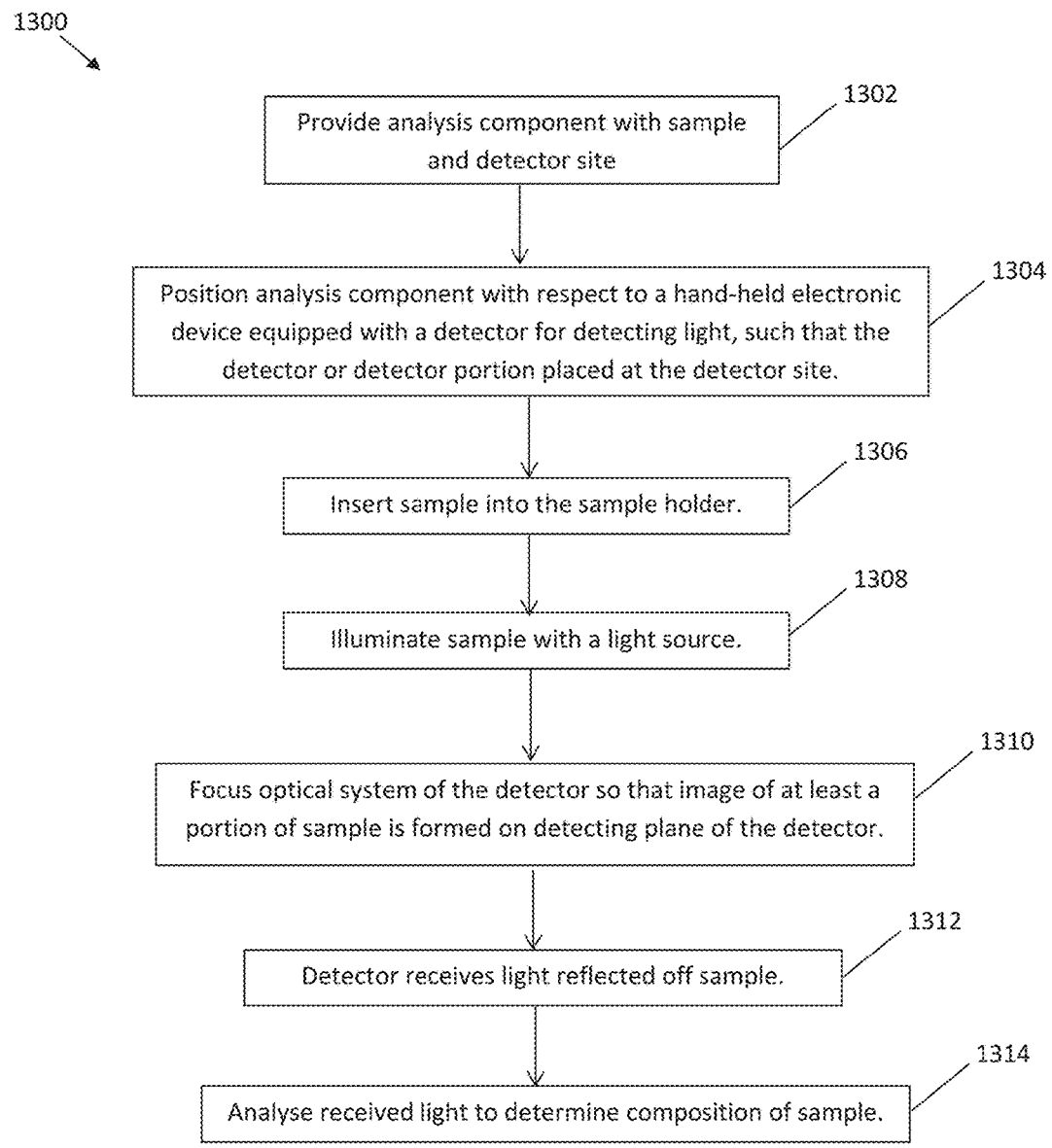
FIG. 13 is a flow chart of a method in accordance with an aspect of the invention.

In addition to the analysis component and system herein described, with reference to FIG. 13, also disclosed is an associated method of analysing a sample.

The method 1300 includes a step 1302 of providing an analysis component having a sample holder for holding the sample and a detector sire at which a detector, or a detector portion of the electronic device, is to be positioned to detect light reflecting off the sample. The detector portion of the device may for instance by an outer lens of a camera. The analysis component may be an analysis component according to any embodiment herein described.

Next, the method 1300 includes the step 1304 of positioning the analysis component with respect to a hand-held electronic device equipped with a detector for detecting light, such that the detector (or portion thereof) is placed at the detector site. The hand-held electronic device may be a smart phone or tablet, or any other electronic device herein described as being suitable for use with embodiments of the analysis component.

In some embodiments, placing the detector or portion thereof at the detector site occurs automatically when the analysis component is attached to the electronic device, for instance, as shown in FIGS. 1 to 6C. This is because in those embodiments, the analysis component is designed to fit to the smartphone in a certain way, and the detector site 118 is located so as to align with the detector or camera 112 of the smartphone. In other embodiments, a user adjusts the position of the analysis component with respect to the smartphone to align the detector site and detector, as illustrated in FIGS. 7 to 9.

The method 1300 then includes the steps of inserting a sample into the sample holder (step 1306), illuminating the sample with a light source (step 1308), and focusing an optical system of the detector such that an image of at least a portion of the sample is formed on a detecting plane of the detector (step 1310). The method then involves using the detector to receive light reflected off the sample (step 1312).

Step 1306 may include inserting a test strip 116 into the sample holder 114 of the analysis component according to various embodiments herein described. Alternatively, step 1306 may include positioning the test strip into a separate sample holder and inserting the sample holder into the slit. Furthermore, step 1306 may include inserting or positioning a sample of a different kind, such as a tube or vial containing a solid, liquid or gas.

Step 1308 can be done with a light source of the smartphone or tablet to illuminate the sample, or using an illuminated user-interface of the smartphone or tablet to illuminate the sample. Alternatively, a LED can be used, such as the LED device 1010 shown in FIGS. 10A and 10B.

Step 1310 may be achieved with the assistance of optical elements, such as high index blocks, lenses etc. provided with the analysis component. In some embodiments, an electronic device such as a smartphone is also configured to auto-focus on an object to be imaged.

With respect to step 1312, the detector can be a camera of the electronic device. Alternatively, the detector can be an IR or UV detector.

Finally, the method includes the step 1314 of analysing the received light to determine a composition of the sample. This can be done by the hand-held electronic device if it is also configured for analysis, such as a smartphone or tablet installed with an appropriate program. Alternatively, the electronic device can be configured to send information regarding the detected light to a further electronic device configured co conduct the analysis. In either respect, as part of the analysis the detected light can be processed to form an image of the sample. The analysis may be colorimetric analysis of the image of the sample, which can involve analysing raw RGB values or HSV values, for example via line scans, as previously described.

According to an embodiment, the method may comprise conducting analysis over a longer period of time, for example over 24 hours. Such analysis may for example be conducted on a urine sample. An example is the measurement of protein or ketones in urine by using test strips. According to an embodiment, the method comprises measuring, using for example an analysis component as herein described, each sample of the urine obtained by separate urinations over a period of 24 hours (or other time period), and using a suitably programmed software application to process the data, for example, by plotting data over time and determining average values. The application can then be programmed co add up the individual measurements taken within a articular time frame and provide a total result at the end of the analysis. Each urine sample may be discarded after it has been analysed. This avoids the need for urine samples to be collected and stored in the same container throughout the 24 hours. The same method can be used to determine small concentration of chemicals in bodily fluids by building up the results and achieving a better signal-to-noise ratio.

It is contemplated that the analysis component, electronic device, and other components or devices of the system disclosed herein may be objects and/or devices in the Internet of Things (IoT). That is, components and device disclosed herein may be wirelessly connected to other devices, for example, to transfer, share, store, monitor and/or access test results. In one example, a secure cloud service that runs the system and provides IoT connectivity with thousands of devices not just smartphones is envisaged.

It will be understood that the method can be applied to analysing a sample in various fields.

Now that various embodiments of the invention have been described, it will be understood to persons skilled in the art that many modifications may be made without departing from the spirit and scope of the invention.

For example, with reference to FIGS. 17A-D another embodiment of system including an analysis component 1700 and smartphone 1710 is shown. In this embodiment, the analysis component 1700 includes a microcontroller chip 1780 that may be used to power LEDs 1782 behind light diffusers 1784 to illuminate the interior of the analysis component 1700 and thus the sample 1716 when used. Different coloured LEDs may be used, for example, one that emits green light. The chip can be used to power multiple devices such as but not limited to thermocouples, vibration sensors, and resistance measurements. The chip may be an Arduino™ chip, a Raspberry Pi™ device or any other suitable chip. The chip 1780 is internally powered by the smartphone 1710 via split cable 1786. The split cable 1786 comprises a device connector 1788 that connects to a power socket of the smartphone 1710, as shown particularly in FIGS. 17A and 17D, and a USB or other connector 1790 to connect to a power source. The split cable 1786 also includes another branch extending from the device connector 1788, which is connectable to the chip 1780, as shown particularly in FIG. 17B. Accordingly, the chip 1780 can be powered as the smartphone 1710 is recharging.

Also, dark coloured or black sample cassettes 1716 instead of a lighter colour can be used to facilitate the detection of light. According to an embodiment, this involves the re-design of current test strips. Dark coloured sample cassettes may be used in contrast to current blood tests that are usually packaged within a white plastic holder. This may provide the advantage of reducing unwanted back scatter. Light-coloured sample cassettes may be redesigned to be a darker colour. Similarly, as shown in FIG. 15B test strips may be redesigned to have a dark coloured background or plastic base. According to another embodiment, the colour of the cassette can be the same as the colour of the fluorescence. For example, if the fluorescence is green the cassette can be green so that other colors are absorbed.

It is also envisioned that sample holders may include but is not limited to zest strip holders, cuvettes, blood test holders etc.

In yet another variation, instead of a predominantly straight optical path from the detector to the sample, the analysis component may comprise various optical components such as mirrors to allow for a "complex" or indirect path of light from the sample to the detector. An example of this is a periscope configuration where multiple mirrors are used to reflect and redirect light. This may provide the advantage of minimising the size of the analysis component. In another example, a tilted Fabry-Pérot interferometer or etalon may be used, which comprises two typically parallel reflecting surfaces for light to travel there through by reflecting off the surfaces.

It is to be understood that, if any prior art publication is referred to herein, such reference does not constitute an admission that the publication forms a part of the common general knowledge in the art, in Australia or any other country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. An analysis system for analyzing a sample, the analysis system comprising:
   a smart device;
   a sample holder for holding the sample relative to the smart device, the sample holder including a component for spacing the sample from a camera or detector of the smart device by a predetermined distance; and
   a mirror configured to divert light reflected off the sample, when held by the sample holder, toward a detecting plane of the camera or detector of the smart device, the detecting plane facing away from the sample holder;

wherein the system is configured to allow light from a light source to illuminate the sample and an image of at least a portion of the sample can be received by the camera or detector of the smart device and wherein the smart device is configured to analyse the image.

2. The analysis system of claim 1, wherein the component is coupled to the smart device.

3. The analysis system of claim 1, wherein the component is separate from the smart device.

4. The analysis system of claim 3, comprising an attachment member for detachably securing the component to the smart device.

5. The analysis system of claim 4, wherein the attachment member comprises a surrounding wall having a slot in which a portion of the smart device is received.

6. The analysis system of claim 1, wherein the component is configured to space the sample holder from the detector site by the predetermined distance such that, in use, the sample is detected at or near a focal length of an optical system associated with, or forming a portion of, the camera or the detector of the smart device.

7. The analysis system of claim 1, wherein the system is configured such that, in use, the detecting plane of the detector or camera of the smart device faces in a direction substantially 90° away from the sample holder.

8. The analysis system of claim 1, wherein the mirror is positioned at an acute angle with respect to a detecting plane of the detector or camera of the smart device.

9. The analysis system of claim 1, wherein the system comprises a window located in a wall of the component or any position along an optical path of the detector or camera of the smart device.

10. The analysis system of claim 1 comprising a divider that, in use, isolates the sample holder from the smart device.

11. The analysis system of claim 10, wherein the component spacing the sample holder from the detector or camera of the smart device is part of the divider.

12. The analysis system of claim 1, wherein the sample holder comprises at least two sample-receiving elements each capable of receiving a sample and being positioned at different distances with respect to the detector or camera of the smart device.

13. The analysis system of claim 12, wherein the at least two sample-receiving elements are in the form of elongate grooves within a component of the sample holder.

14. The analysis system of claim 1, comprising a reflecting grating positioned with respect to the sample holder such that in use when the sample is illuminated, an image of the sample is projected onto the reflection grating, thus forming a spectrum of the image to be analysed.

15. The analysis system claim 1, wherein the depth of the component is of smaller dimension than both the length and width of the component.

16. The system of claim 1, wherein a portion of sample holder and the component define a first plane, and a detecting plane of the detector or camera is substantially parallel to the first plane.

17. The system of claim 16, wherein the component and the smart device each have a longitudinal axis, and the component is positioned with respect to the electronic device such that the longitudinal axis of the component is substantially parallel or substantially perpendicular with the longitudinal axis of the smart device.

18. The system of claim 16, wherein the detector or camera detects infra-red light or visible light reflected off the sample.

19. A method of analysing a sample, comprising:
providing a sample;
inserting a sample into the sample holder;
providing the system according to any one of the preceding claims;
positioning sample holder the smart device relative to each other such that the component of the sample holder spaces the sample from a camera or detector of the smart device by a predetermined distance;
illuminating the sample with a light source;
focusing an optical system of the detector or camera or detector of the smart device such that an image of at least a portion of the sample is formed on a detecting plane of the detector or camera;
using the detector or camera to receive an image reflected off the sample; and
analysing the received image to determine a composition of the sample.

20. The method of claim 19, wherein analysing the received light comprises performing colorimetric analysis on the image of the sample.

* * * * *